(12) United States Patent
Yamasaki et al.

(10) Patent No.: US 7,947,656 B2
(45) Date of Patent: May 24, 2011

(54) PROCESSES FOR PRODUCING CELLOOLIGOSACCHARIDE

(75) Inventors: Naoaki Yamasaki, Nobeoka (JP); Ichiro Ibuki, Nobeoka (JP); Koji Isaka, Izunokuni (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 846 days.

(21) Appl. No.: 11/632,696

(22) PCT Filed: Jul. 26, 2005

(86) PCT No.: PCT/JP2005/013647
§ 371 (c)(1),
(2), (4) Date: Jan. 18, 2007

(87) PCT Pub. No.: WO2006/011479
PCT Pub. Date: Feb. 2, 2006

(65) Prior Publication Data
US 2007/0207108 A1    Sep. 6, 2007

(30) Foreign Application Priority Data

Jul. 27, 2004 (JP) ................................ 2004-218902
Nov. 8, 2004 (JP) ................................ 2004-323579
Apr. 25, 2005 (JP) ................................ 2005-125966

(51) Int. Cl.
*A61K 31/715* (2006.01)
*A61K 8/73* (2006.01)
*C12P 19/04* (2006.01)

(52) U.S. Cl. ..................... 514/23; 424/70.13; 435/101

(58) Field of Classification Search ................ None
See application file for complete search history.

(56) References Cited

U.S. PATENT DOCUMENTS
2005/0277172 A1 * 12/2005 Day et al. ................... 435/69.1

FOREIGN PATENT DOCUMENTS

| | | |
|---|---|---|
| EP | 0 382 577 | 8/1990 |
| JP | 62-273921 | 11/1987 |
| JP | 1-256394 | 10/1989 |
| JP | 4-281759 | 10/1992 |
| JP | 5-115293 | 5/1993 |
| JP | 5-227957 | 9/1993 |
| JP | 5-227958 | 9/1993 |
| JP | 5-317073 | 12/1993 |
| JP | 6-503960 | 5/1994 |
| JP | 7-184678 | 7/1995 |
| JP | 8-89274 | 4/1996 |
| JP | 8-308589 | 11/1996 |
| JP | 9-107087 | 4/1997 |
| JP | 2001-95594 | 4/2001 |
| JP | 2001-112496 | 4/2001 |
| JP | 2003-212888 | 7/2003 |
| JP | 2005-68140 | 3/2005 |
| KR | 2001-0032777 | 4/2001 |

OTHER PUBLICATIONS

Akpinar O. et al., "Journal of Agricultural and Food Chemistry", 52(13), pp. 4144-4148, (2004).
Canadian Office Action issued Dec. 7, 2009 in corresponding Canadian Patent Application 2,575,237.
Takashi Watanabe "Development of physiological function of Cellooligosaccharides," Cellulose Comunication, vol. 5, No. 2, 1998, 91-97.
"Cellulase" published by Kodansha Scientific, 97-104 (1987).
Tanaka Mitsuo et al., "Efficient Continuous Production of Cellobiose by Hydrolysis of Crystalline Cellulose with Cellulase" , Chemical Engineering Reports, Japan, 2000, vol. 26(3), p. 413-417.
Wilke Charles R. et al., "Studies of Cellulose as a Chemical and Energy Resource: Production of Supplementary Enzymes for Cellobiose and Liginin as Aid to Cellulose Hydrolysis" PB Report, 1975, PB-271229.
International Search Report of International Application (mailed Oct. 25, 2005) PCT/JP2005/013647, filed Jul. 26, 2005.
Liming Xia, et al, "Research on preparation of active cellooligosaccharide by enzyme", Journal of Zhejiang University, Engineering Science, vol. 4, p. 381, passage 1.
Chinese Office Action issued on Jul. 17, 2009 in corresponding Chinese Patent Application 200580025354.0.
Sangseethong K. et al., "Rationale for particle size effect on rates of enzymatic saccharification of microcrystalline cellulose", Journal of Food Biochemistry, 1998, vol. 22, No. 4, Jan. 1, 1998, pp. 321-330.
Bonnin E. et al., "Enzymic release of cellobiose from sugar beet pulp, and its use to flavor vanillin production in *Pycnoporus cinnabarinus* from vanillic acid", Carbohydrate Polymers, Applied Science Publishers, Ltd., vol. 41, No. 2, Feb. 1, 2000, pp. 143-151.
Peters L. E. et al., "The Impact of Initial Particle Size on the Fragmentation of Thermomonspora-Fusca", Bioresource Technology, vol. 35, No. 3, 1991, pp. 313-320.
Mishra S. et al., "Isolation and Characterization of a Mutant of *Trichoderma Reesi* Showing Reduced Levels of Extracellular Beta-Glucosidase", Journal of General Microbiology, Society for Microbiology, Reading, GB, vol. 135, No. 12, Dec. 1, 1989, pp. 3459-3465.
Lee S. E. et al., "A Theoretical Model for Enzymatic Hydrolysis of Cellulose" Biotechnology and Bioengineering, vol. 20, No. 1, 1978, pp. 141-144.
Japanese Office Action for corresponding Japanese Application No. 2005-125975, mailed on Nov. 30, 2010.
Korean Patent Office Action, mailed Jul. 3, 2008 and issued in a corresponding Korean Patent Application.
European Search Report dated Jul. 5, 2010 and issued in corresponding European Patent Application 05767248.7.
References AG-AI are cited in the Japanese Office Action for corresponding Japanese Application No. 2005-125975 (Reference BE).

* cited by examiner

Primary Examiner — Lisa J Hobbs
(74) Attorney, Agent, or Firm — Staas & Halsey LLP

(57) ABSTRACT

A process of producing cellooligosaccharide, comprising enzymatically decomposing, in the presence of cellulase, a water-insoluble natural cellulosic material having an average degree of polymerization not greater than 700, an average particle size not greater than 100. A process of producing cellooligosaccharide, comprising enzymatically decomposing, in the presence of cellulase, a water-insoluble natural cellulosic material having an average degree of polymerization not greater than 700, containing 10% or more by mass of a colloidal cellulose component and a diethyl ether-soluble substance content less than 1% by mass.

11 Claims, 2 Drawing Sheets

PROCESSES FOR PRODUCING CELLOOLIGOSACCHARIDE

CROSS REFERENCE TO RELATED APPLICATIONS

This application is based on PCT Application No. PCT/JP2005/013647 filed Jul. 26, 2005, and Japanese Application No(s). 2004-218902, 2004-323579 and 2005-125966, filed Jul. 27, 2004, Nov. 8, 2004 and Apr. 25, 2005 respectively in Japan, the disclosures of which are hereby incorporated herein by reference.

TECHNICAL FIELD

The present invention relates to a process of obtaining cellooligosaccharide by enzymatically decomposing a cellulosic material. The present invention particularly relates to a process by which a water-insoluble natural cellulosic material whose average degree of polymerization, average particle size, colloidal cellulose component content, and diethyl ether-soluble substance content are controlled to fall within a certain range is used as a substrate and enzymatically decomposed with cellulase whose activity ratio of β-glucosidase activity to crystalline cellulose-decomposing activity (β-glucosidase activity/crystalline cellulose-decomposing activity) is controlled to fall within a certain range, thereby enhancing the decomposition rate of cellulose in a short time to selectively produce cellooligosaccharide in high yields.

BACKGROUND ART

Cellooligosaccharide is a general term for cellobiose, cellotriose, cellotetraose, cellopentaose, and cellohexaose and is one of oligosaccharides where 1 to 6 glucopyranose units are joined together through β-1,4 linkages.

In recent years, the physiological function of the cellooligosaccharide is being elucidated as with other oligosaccharides. Therefore, the cellooligosaccharide is expected as a novel raw material for functional foods (Non-Patent Document 1).

The cellooligosaccharide is obtained by hydrolyzing its polymer, cellulose, with an enzyme. However, naturally-occurring cellulose is hardly soluble in water and highly crystalline and is therefore less likely to undergo enzymatic decomposition by cellulase. Thus, this has presented a problem.

In the enzymatic decomposition reaction of cellulose, cellooligosaccharide obtained as a decomposition product is further decomposed into glucose units by β-glucosidase that is a component in cellulase, thereby causing reduction in the yield of cellooligosaccharide. Thus, this has presented another problem (Non-Patent Document 2).

In light of the above-described problems, many attempts have heretofore been made for the purpose of improving the yield of cellooligosaccharide at the time when cellulose is enzymatically decomposed.

Processes of producing cellooligosaccharide using particular cellulose include the followings:

Patent Document 1 has described a process of producing cellooligosaccharide, in which a cellulose raw material containing amorphous cellulose in large amounts is used and subjected to hydrolysis reaction with cellulase in the presence of lignin while at least cellobiose of cellooligosaccharides generated by the hydrolysis reaction is collected from the reaction solution at any time.

Patent Document 2 has described a process of producing cellooligosaccharide, in which wet pulp, which is obtained without undergoing drying after the cooking of a natural lignocellulose-containing raw material, is partially hydrolyzed with cellulase to collect at least cellobiose of generated cellooligosaccharides. In these production processes, cellooligosaccharide-decomposing enzyme β-glucosidase contained in cellulase is adsorbed into lignin and inhibited from action of β-glucosidase, thereby reducing the decomposition of the cellooligosaccharide into glucose to enhance the reaction selectivity of cellooligosaccharide. However, in these production processes, the resulting saccharification liquid contains lignin in large amounts, with the result that the yield of cellooligosaccharide is reduced. Moreover, because treatment for eliminating lignin from the saccharification liquid is required for obtaining cellooligosaccharide of high purity, a complicated purification step has been a problem.

Patent Document 3 has described a process of producing cellobiose, a type of cellooligosaccharide, by reacting lignocellulose containing 1 to 20% by mass of lignin with cellulase and a lignin-decomposing fungus such as a white-rot fungus. This process can enhance the action of cellulase on the substrate without treatment for eliminating lignin in cellulose. However, its decomposition product contains not only cellobiose but also lignin decomposition products, thereby causing reduction in the yield of cellooligosaccharide as in the above-described processes. Moreover, because a step of removing the lignin decomposition products is required for obtaining cellobiose of high purity, a complicated purification step has been a problem.

Patent Document 4 has described a process of producing cellooligosaccharide, in which, after cellulase is added to a cellulose solution obtained by dissolving cellulose in solvents such as amine oxide, lithium chloride/N,N-dimethylacetamide, cuprammonium, and viscose, cellulase-containing regenerated cellulose is obtained from the resulting solution and subsequently subjected to enzymatic reaction by the cellulase contained in the regenerated cellulose in the presence of a buffer to produce cellooligosaccharide. The process does not require special pretreatment such as purification given to cellulase and improves the yield of cellooligosaccharide. However, because the process requires a step of dissolving and regenerating cellulose, a complicated step has been a problem. Chemical substances used in the dissolution of cellulose, such as amine oxide, lithium chloride/N,N-dimethylacetamide, cuprammonium, and viscose, have no small action on cellulase. As a result, there has been a problem in that decomposition reaction of cellulose is affected by the chemical substances.

Patent Document 5 has described a process of producing cellobiose using, as a raw material, bleached slush pulp having water retentivity between 230 and 280% and drainability between 550 and 640 ml. The slush pulp used therein is undried pulp after cooking/bleaching treatment. Although the use of the pulp as a raw material certainly improves the production quantity of cellobiose, undried slush pulp is restricted in substrate concentration at the time of enzymatic decomposition due to its high water retentivity. Thus, the poor productivity of cellooligosaccharide has been a problem.

Patent Document 6 has described a process in which, after a cellulose component is solubilized from a cellulose-containing material using supercritical or subcritical water, the resulting treated liquid is supplemented with a cellulase preparation, and cellulose and cellooligosaccharide (partial decomposition product of cellulose) having a high degree of polymerization are hydrolyzed with the cellulase preparation, thereby obtaining glucose and/or cellooligosaccharide. This process improves both of the production quantity and the yield of cellooligosaccharide such as cellobiose and cellotriose. However, there remains an issue surrounding the safety of cellulose pretreatment, for example, the safety of facilities such as pressure-resistant/acid-resistant facilities required for supercritical or subcritical water treatment and the safety against pressurization and heating.

Patent Document 7 has described a process of producing cellooligosaccharide using, as a reaction substrate for cellulase, pulp having a degree of cellulose I crystallization from 10% to 80% determined by X ray diffractometry and water retentivity from 200% to 1000%, wherein the pulp is subjected to any one or several treatment(s) selected from fibrillation treatment, mechanochemical treatment, and chemical treatment. The process improves the production quantity of cellobiose and the decomposition rate of cellulose. However, because of use of fibrous pulp with high water retention as cellulose the process presents such a problem of poor productivity of cellooligosaccharide that clogging occurs, substrate concentration is restricted, and so on at each producing step such as pretreatments (e.g. fibrillation treatment, mechanochemical treatment, and chemical treatment) and, the subsequent enzymatic decomposition and purification of oligosaccharides. The process is essentially different from the process of the present invention in which an average degree of polymerization, an average particle size, a colloidal component content, and so on, are controlled at high level and treating properties at each step including enzymatic decomposition are enhanced.

Methods for improving the yield of cellooligosaccharide by enzymatically decomposing cellulose with particular cellulase include the following Patent Documents 8 to 11:

Patent Document 8 has described a process of producing cellooligosaccharide from a cellulosic material in an aqueous reaction solution by the action of cellulase produced by a microorganism belonging to the genus *Cellvibrio*, in which an ultrafiltration reactor is used in combination, so that production inhibition is removed to produce and accumulate cellooligosaccharide. According to this process, cellooligosaccharides consisting only of cellobiose and cellotriose are obtained as decomposition products from the enzymatic decomposition of the cellulosic material. However, because an enzyme produced by a microorganism of the genus *Cellvibrio* is less likely to act on crystalline cellulose, amorphous cellulose as a substrate is required for reducing reaction time and improving yields. Thus, a complicated step has been a problem.

Patent Document 9 has described a process of producing cellooligosaccharide by decomposing cellulose with cellulase, in which cellulase is brought in advance into contact with a weakly acidic cation-exchange resin equilibrated to pH 3.5 to 5.0 to thereby selectively remove β-glucosidase in the cellulase, and the cellulase from which β-glucosidase has been removed is brought into contact with cellulose. According to the process, glucose is reduced by the enzymatic decomposition of the cellulose, so that a decomposition product having 60% or more cellooligosaccharide can be obtained. However, the above-described method requires a step of removing β-glucosidase in cellulase. Thus, there has been a problem in that a step of producing cellooligosaccharide is complicated. Moreover, because this step of purifying cellulase requires the amount of a cation-exchange resin 75 to 1000 times greater than that of untreated cellulase, the amount of cellulase treated is limited and the productivity of cellooligosaccharide is not sufficient. Thus, there has been a problem in that the cost of cellulase purification and the cost of separation/purification agents of the cation-exchange resin are high.

Patent Document 10 has described a process for cellulase purification in which, after cellulase is dissolved along with either or both of cellulose ester or(and) cellulose ether ester and incubated for a fixed period of time, pH is changed and an insolubilized solid fraction is separated from the solution to thereby selectively remove β-glucosidase in the cellulase; and a process for cellobiose production in which cellulose together with the cellulase from which β-glucosidase has been removed is added to an aqueous medium to make a suspension which is in turn incubated for a fixed period of time to produce cellobiose into the suspension, followed by the collection of the cellobiose.

Patent Document 11 has described a process for cellulase purification in which, after chitosan and cellulase are dissolved in an aqueous medium whose pH has been adjusted to pH that renders the chitosan soluble and are incubated for a fixed period of time, pH is changed and an insolubilized solid fraction is separated from the solution to thereby selectively remove β-glucosidase in the cellulase; and a process for cellobiose production in which cellulose together with the cellulase from which β-glucosidase has been removed is added to an aqueous medium to make a suspension which is in turn incubated for a fixed period of time to produce cellobiose into the suspension, followed by the collection of the cellobiose. These processes improve the yield of cellobiose by subjecting cellulase to adsorption/separation treatment with a cellulose derivative or chitosan and bringing cellulose into contact with the cellulase that remains adsorbed in the cellulose derivative or chitosan. However, these processes require treatment for purifying cellulase and therefore complicate a producing step. There has been a problem in that high costs are needed because the cellulose derivative and the chitosan used in the purification of cellulase are expensive. Moreover, since the cellulase is used with the cellulose derivative and the chitosan in the enzymatic decomposition of cellulose, there has also been a problem in that a step of removing them from the decomposition reaction solution is required.

Heretofore, a process has not been known, by which a water-insoluble natural cellulosic material whose average degree of polymerization, average particle size, colloidal cellulose component content, and diethyl ether-soluble substance content are controlled by pretreatment to fall within a certain range is used as a substrate and enzymatically decomposed with cellulase whose activity ratio of β-glucosidase activity to crystalline cellulose-decomposing activity (β-glucosidase activity/crystalline cellulose-decomposing activity) is controlled to fall within a certain range, thereby enhancing the decomposition rate of cellulose in a short time to selectively produce cellooligosaccharide in high yields.

[Non-Patent Document 1] Cellulose Communications, 5, No 2, 91-97 (1998)
[Non-Patent Document 2] "Cellulase" published by Kodansha Scientific, 97-104 (1987)
[Patent Document 1] JP-A-05-317073
[Patent Document 2] JP-A-07-184678
[Patent Document 3] JP-A-08-89274
[Patent Document 4] JP-A-08-308589
[Patent Document 5] JP-A-09-107087
[Patent Document 6] JP-A-2001-95594
[Patent Document 7] JP-A-2005-68140
[Patent Document 8] JP-A-01-256394
[Patent Document 9] JP-A-05-115293
[Patent Document 10] JP-A-05-227957
[Patent Document 11] JP-A-05-227958

DISCLOSURE OF THE INVENTION

An object of the present invention is to selectively produce cellooligosaccharide in high yields by enzymatically decomposing a water-insoluble natural cellulosic material used as a raw material in the presence of particular cellulase, thereby enhancing the decomposition rate of cellulose in a short time.

The present inventors have completed the present invention by finding out that, for solving the above-described problems, a water-insoluble natural cellulosic material whose average degree of polymerization, average particle size, colloidal cellulose component content, and diethyl ether-soluble substance content are controlled to fall within a certain range is used as a raw material and enzymatically decomposed with cellulase having particular activity, thereby enhancing the decomposition rate of cellulose in a short time to selectively give cellooligosaccharide in high yields.

Thus, the present invention is as follows:

(1) a process of producing cellooligosaccharide, comprising enzymatically decomposing, in the presence of cellulase, a water-insoluble natural cellulosic material having an average degree of polymerization not greater than 700, an average particle size not greater than 100 μm, and a diethyl ether-soluble substance content less than 1% by mass;

(2) a process of producing cellooligosaccharide, comprising enzymatically decomposing, in the presence of cellulase, a water-insoluble natural cellulosic material having an average degree of polymerization not greater than 700, containing 10% or more by mass of a colloidal cellulose component and a diethyl ether-soluble substance content less than 1% by mass;

(3) the process of producing cellooligosaccharide according to (1) or (2), wherein the above-described water-insoluble natural cellulosic material has an average particle size not greater than 100 μm and contains 10% or more by mass of a colloidal cellulose component;

(4) the process of producing cellooligosaccharide according to any one of (1) to (3), wherein the above-described water-insoluble natural cellulosic material has an average degree of polymerization not greater than 500 and an average particle size not greater than 50 μm;

(5) the process of producing cellooligosaccharide according to any one of (1) to (4), wherein the above-described water-insoluble natural cellulosic material has an average degree of polymerization not greater than 400 and an average particle size not greater than 30 μm;

(6) the process of producing cellooligosaccharide according to any one of (1) to (5), wherein the above-described water-insoluble natural cellulosic material contains 15% or more by weight of a colloidal cellulose component;

(7) the process of producing cellooligosaccharide according to any one of (1) to (6), wherein the above-described cellulase has an activity ratio (β-glucosidase activity/crystalline cellulose-decomposing activity at a temperature of 55° C.) not greater than 0.7;

(8) the process of producing cellooligosaccharide according to (7), wherein the above-described cellulase has an activity ratio not greater than 0.5;

(9) the process of producing cellooligosaccharide according to (8), wherein the above-described cellulase has an activity ratio not greater than 0.35;

(10) the process of producing cellooligosaccharide according to any one of (1) to (9), wherein the above-described diethyl ether-soluble substance is lignin;

(11) the process of producing cellooligosaccharide according to any one of (1) to (10), wherein the above-described water-insoluble natural cellulosic material contains a cellulose I crystal;

(12) the process of producing cellulase according to any one of (1) to (11), wherein the above-described enzymatic decomposition is performed by culturing cellulase-producing microorganism, wherein an activity ratio of β-glucosidase activity to crystalline cellulose-decomposing activity (β-glucosidase activity/crystalline cellulose-decomposing activity at a temperature of 40° C.) in a culture solution obtained by culturing the above-described cellulase-producing microorganism is not greater than 0.5;

(13) the process of producing cellulase according to (12), wherein the above-described activity ratio of β-glucosidase activity to crystalline cellulose-decomposing activity is not greater than 0.35;

(14) the process of producing cellulase according to any one of (12) or (13), wherein the above-described cellulase-producing microorganism is a strain selected and thereby obtained as a strain reduced in β-glucosidase production;

(15) the process of producing cellulase according to any one of (12) to (14), wherein pH during culture is controlled at less than 3.5 when the above-described cellulase-producing microorganism is cultured;

(16) the process of producing cellulase according to any one of (12) to (15), wherein the above-described cellulase-producing microorganism is a strain belonging to the genus *Trichoderma*;

(17) cellooligosaccharide characterised in that diethyl ether-soluble substance content is 2000 ppm or less;

(18) cellooligosaccharide obtainable by the process according to any one of claims 1 to 11, characterised in that diethyl ether-soluble substance content is 2000 ppm or less;

(19) cellooligosaccharide according to claim 18, wherein the diethyl ether-soluble substance content is 1000 ppm or less;

(20) a food, cosmetic, or pharmaceutical preparation, characterised by comprising cellooligosaccharide obtainable by the process according to any one of claims 1 to 11; and

(21) a food, cosmetic, or pharmaceutical preparation, characterised by comprising cellooligosaccharide according to claim 17 or 18.

According to the process of producing cellooligosaccharide of the present invention by enzymatically decomposing a water-insoluble natural cellulosic material, the decomposition rate of cellulose can be enhanced in a short time and cellooligosaccharide can selectively be produced in high yields.

BEST MODE FOR CARRYING OUT THE INVENTION

Figure 1:
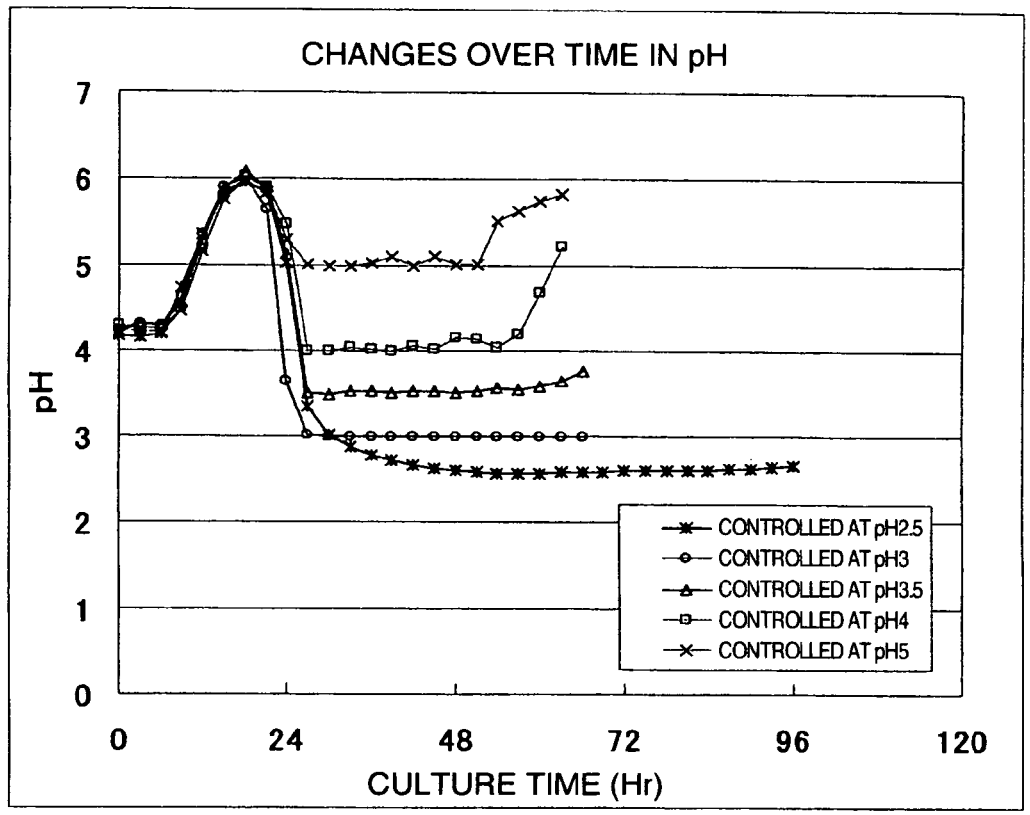
FIG. 1 is a graph showing changes over time in pH during culture in Examples 13 and 14 and Comparative Example 6.

Hereinafter, the present invention will be described in detail with particular emphasis on its preferred aspects.

A natural cellulosic material used in the present invention is a naturally-occurring water-insoluble fibrous substance containing cellulose. The natural cellulosic material may be derived from plants or animals. Examples of the animals and plants for producing it include woods, bamboos, straws, rice straws, cotton, ramie, bagasse, kenaf, beet, sea squirts, and bacterial cellulose. One of these natural cellulosic materials may be used alone as a raw material, or alternatively two or more of them may be mixed and used as a raw material.

The cellulosic material used in the present invention needs to be a natural cellulosic material. Natural cellulose and regenerated cellulose can be discriminated by their crystal forms. The natural cellulosic material of the present invention needs to contain a cellulose I crystal and have its content of 1% or more. A more preferable cellulose I crystal content is 50% or more. The cellulose I crystal form used herein can be distinguished by an X-ray diffraction pattern obtained by wide-angle powder X-ray diffractometry (manufactured by Rigaku, trade name: Rotaflex RU300). Its content is expressed as a percentage of the peak area of the cellulose I crystal to the total peak area of a diffraction image obtained by X-ray diffraction. A cellulosic material in a dry state subjected to wide-angle powder X-ray diffraction measurement may be pulverize by a method known in the art and then used in the measurement, whereas a cellulosic material in a wet state can be dried by a method known in the art, then pulverized, and used in the measurement. A higher cellulose I crystal content is preferred because a cellulosic material close to natural cellulose is used in enzymatic decomposition and an artificial chemical treatment step such as regeneration treatment for cellulose is simplified. The highest cellulose I crystal content is not particularly limited and however, is less than 99% in light of the composition of natural cellulose currently known.

The natural cellulosic material used in the present invention is water-insoluble. "Water-insoluble" used herein means that 90% or more by mass of a water-insoluble component is contained in the natural cellulosic material. This water-insoluble component is obtained by dispersing the cellulosic material in pure water at 25° C. and removing a water-soluble component by ultrafiltration (molecular weight cut-off: 10000), followed by the quantification of a water-insoluble residue.

The water-insoluble natural cellulosic material in the present invention has an average degree of polymerization not greater than 700. The average degree of polymerization used herein can be measured by a reduced specific viscosity method with a copper ethylenediamine solution specified by Confirmatory Test for Crystalline Cellulose (3) in "the Japanese Pharmacopoeia, 14th Edition" (published by Hirokawa Publishing). Since the cellulosic material having an average degree of polymerization not greater than 700 is more likely to undergo physical treatment such as stirring, crushing, and grinding, the amount of its colloidal component can readily be controlled. When the average degree of polymerization of the water-insoluble natural cellulosic material is controlled to fall within the above-described range, a fiber in the cellulosic material is rendered porous. Therefore, the possibility of enzyme-substrate contact is increased and the decomposition rate of cellulose is improved when the cellulosic material is enzymatically decomposed. The average degree of polymerization is preferably not greater than 500, more preferably not greater than 400. A smaller average degree of polymerization allows the easier control of the amount of a colloidal component and the decomposition rate. Thus, the smallest average degree of polymerization is not particularly limited and however, is preferably more than 10 in light of the range of an average degree of polymerization obtained by convenient procedures.

The water-insoluble natural cellulosic material used in the present invention has an average particle size not greater than 100 µm. The average particle size used herein refers to the 50% accumulated particle size in volume/frequency particle size distribution obtained as follows: The cellulosic material is made into an aqueous emulsion of a concentration of 0.2% by mass and dispersed therein by means of a high shear homogenizer (manufactured by NIPPON SEIKI CO., LTD., trade name, Excel Auto Homogenizer ED-7, treatment conditions: at a speed of 5000 rpm for 3 minutes) and, after the pH of the dispersion was adjusted to 7.5-8.5, subjected to a centrifuge (manufactured by KUBOTA Corporation, trade name, 6930 Centrifuge, treatment conditions: centrifugal force 2000 G for 5 minutes), after which the dispersion is separated to the supernatant component and the sedimentation component and the ratios by weight of the respective components are measured. The volume/frequency particle size distributions of the respective components are obtained using water as a medium by laser diffractometry (manufactured by Horiba, trade name LA-910, ultrasonication for 1 min) and multiplied by the ratio by weight of the supernatant component and the sedimentation component to obtain the 50% accumulated particle size in volume/frequency particle size distribution. An average particle size not greater than 100 µm is preferred because the contact area (accessibility) of the cellulose to cellulase is increased in the enzymatic decomposition of the cellulose, so that the production rate and yield of cellooligosaccharide are improved. The average particle size is more preferably not greater than 50 µm, particularly preferably not greater than 30 µm, still more preferably not greater than 10 µm. A smaller average particle size attains more improvement in the production rate, production selectivity, and yield of cellooligosaccharide. Therefore, the smallest average particle size is not particularly limited and however, is not smaller than 0.01 µm in light of the range of an average particle size obtained by convenient procedures.

The water-insoluble natural cellulosic material used in the present invention needs to contain 10% or more by mass of a colloidal cellulose component. The colloidal cellulose component used herein is expressed as a percentage of a cellulose solid content remaining in a supernatant after centrifugation, which is obtained by dispersing a water suspension having 0.2% by mass concentration of the natural cellulosic material with a high-shear homogenizer (manufactured by Nippon Seiki, trade name: Excel Auto Homogenizer ED-7, Treatment conditions: at a speed of 5000 rpm for 3 minutes) and adjusting its pH to 7.5 to 8.5, followed by centrifugation (manufactured by Kubota Corp., trade name: Centrifuge Model 6930, treatment conditions at a centrifugal force of 2000 G for 5 minutes). A colloidal cellulose component content of 10% or more by mass allows improvement in the production rate, production selectivity, and yield of cellooligosaccharide. The colloidal cellulose component content is more preferably 15% or more by mass, particularly preferably 40% or more by mass. The amount of this colloidal cellulose component is a factor that affects enzymatic decomposability independently of the average particle size of the cellulosic material. Although the mechanism of the amount of the colloidal cellulose component for improvement in the production rate, selectivity, and yield of cellooligosaccharide is not clear, it is probable that an increased amount of the colloidal cellulose component allows the stabilized suspension of the cellulose as a substrate and the uniform contact of the enzyme and the substrate, thereby improving the above-described enzymatic decomposability. A higher colloidal cellulose component content attains more improvement in the enzymatic decomposability. Therefore, the highest colloidal cellulose component content is not particularly limited and however, is not higher than 99.9% by mass in light of a range achieved by convenient pretreatment.

The water-insoluble natural cellulosic material used in the present invention has a diethyl ether-soluble substance content less than 1% by mass. The diethyl ether-soluble substance content used herein refers to impurities in the cellulosic material that are soluble in diethyl ether, such as lignin and lignin decomposition products, and can be measured by a method of quantifying a diethyl ether-soluble substance specified by Purity Test for Crystalline Cellulose (2) in "the Japanese Pharmacopoeia, 14th Edition" (published by Hirokawa Publishing). The use of cellulose of high purity having a lignin content less than 1% by mass more improves the purity of cellooligosaccharide obtained by enzymatic decomposition. The improved purity of cellooligosaccharide results in improvement in production yield, thereby facilitating the purification of cellooligosaccharide and the collection of cellulase after enzymatic decomposition. The diethyl ether-soluble substance content is more preferably 0.5% or less by mass, still more preferably 0.3% or less by mass. A lower diethyl ether-soluble substance content attains more improvement in the above-described purity of cellooligosaccharide. Therefore, the lowest colloidal cellulose component content is not particularly limited and however, is not lower than 0.0005% by mass in light of the range of a lignin content achieved by convenient pretreatment.

Preferred treatment methods by which the average degree of polymerization, average particle size, colloidal cellulose component content, and diethyl ether-soluble substance content of the natural cellulosic material satisfy the scope of the present invention include the followings:

No particular limitation is imposed on a method of controlling the average degree of polymerization and the diethyl ether-soluble substance content as long as the method is known in the art. One example thereof includes hydrolysis treatment. This hydrolysis treatment is preferred because amorphous cellulose and hemicellulose and impurities (such as lignin) within the cellulose fiber are removed to render the interior of the fiber porous, into which cellulase is therefore more likely to infiltrate at the time of enzymatic decomposition, thereby improving both of the decomposition rate of cellulose and the yield of cellooligosaccharide.

Moreover, the hydrolysis is preferred because, when the hydrolyzed cellulosic material is further treated by a method known in the art, the cellulosic material is more likely to undergo mechanical treatment because of its porous fibrous interior and the average particle size and colloidal component content of the cellulosic material are readily controlled.

A method for hydrolysis is not particularly limited and however, is exemplified by acid hydrolysis, alkaline oxidative decomposition, hydrothermal decomposition, steam explosion, and microwave decomposition. Any of these methods may be used alone, or otherwise two or more of them may be combined. When acid hydrolysis of the above-described methods is performed, the average degree of polymerization can readily be controlled by adding an appropriate amount of protonic acid, carboxylic acid, Lewis acid, heteropolyacid, and the like to the cellulosic material that remains dispersed in an aqueous medium and heating the resulting mixture with stirring. In this case, reaction conditions such as temperature, pressure, and time differ depending on the type and concentration of cellulose as well as the type and concentration of acid and however, are appropriately adjusted to achieve an average degree of polymerization of interest. For example, for the above-described acid hydrolysis, preferred are such reaction conditions that the cellulose is treated with 1% or less by mass of a mineral acid solution under pressure at 100° C. or higher for 10 minutes or more. This is because a catalytic component such as acid infiltrates into the interior of the cellulose fiber to promote hydrolysis, so that the amount of the catalytic component used is reduced.

A method of controlling the average particle size and the colloidal cellulose component content is not particularly limited as long as the method is known in the art. One example thereof includes grinding, crushing, sieve classification, cyclones, and centrifugation using a centrifuge. These methods may be used alone, or otherwise two or more of them may be combined. These methods may be conducted as both wet and dry processes. Cellulosic materials individually obtained by the wet process may be mixed together prior to enzymatic decomposition, while cellulosic materials individually obtained by the dry processes may be mixed together prior to enzymatic decomposition. Or otherwise, cellulosic materials obtained by the wet process may be combined with those obtained by the dry process.

For example, when the cellulose is treated by the wet process, the average particle size or colloidal cellulose component content of the cellulosic material can readily be adjusted by subjecting a cellulose dispersion containing 1 to 99% cellulosic material and a medium to grinding, crushing, or the like, known in the art. In this case, the medium used is not particularly limited and includes water, alcohols such as methanol, ethanol, n-propyl alcohol, isopropyl alcohol, butyl alcohol, 2-methylbutyl alcohol, and benzyl alcohol, hydrocarbons such as pentane, hexane, heptane, and cyclohexane, and ketones such as acetone and ethyl methyl ketone. In particular, a preferred organic solvent is any of those used at a step of producing pharmaceuticals, foods, and additives thereof and includes those classified as solvents in "Dictionary of Pharmaceutical Additives" (published by Yakuji Nippo), and "Japanese Pharmacopoeia" and "Official Method for Food Additives" (published by Hirokawa Publishing). Water and the organic solvents may be used alone, or two or more of them may be used in combination. Alternatively, after one medium is used in dispersion and then removed, the cellulosic material may be dispersed again in a different medium.

A grinding method includes: a grinding method using stirring blades such as unidirectional rotary-, multi-axis rotary-, reciprocal inverse-, vertical motion-, rotary and vertical motion-, and duct line-system stirring blades, such as portable mixers, solid mixers, and lateral mixers; a jet-system stirring grinding method such as line mixers; a grinding method using high-shear homogenizers, high-pressure homogenizers, ultrasonic homogenizers, and the like; a rotary extrusion-system grinding method using kneaders; and a grinding method combining consolidation with shearing, such as roll mills, ball mills, vibratory ball mills, and bead mills, any method of which may be used alone or in combination.

A crushing method includes a screen-system crushing method such as screen mills and hammer mills; a bladerotating shear screen-system crushing method such as flash mills; an air jet-system crushing method such as jet mills; a crushing method combining consolidation with shearing, such as roll mills, ball mills, vibratory ball mills, and bead mills; and a stirring blade-system crushing method, any method of which may be used alone or in combination.

Cellulase of the present invention is a general term for cellulose-decomposing enzymes. Any of those having the activity of decomposing cellulose is encompassed in the cellulase according to the present invention. Examples of cellulase enzyme sources include cellulase-producing live microorganisms themselves or culture supernatant liquids thereof, purified enzymes from enzymes produced by the cellulase-producing live microorganisms, or preparations made from the purified enzymes along with additives such as excipients and stabilizers. When the cellulase preparation is used in enzymatic decomposition, the additive added to the preparation is not particularly limited. Its dosage form may be any of a powder, a granule, a liquid, and the like.

The origin of the cellulase is not particular limited and can include cellulase produced by cellulase-producing microorganisms known in the art such as microorganisms of the genus *Trichoderma*, the genus *Acremonium*, the genus *Aspergillus*, the genus *Bacillus*, the genus *Pseudomonas*, the genus *Penicillium*, the genus *Aeromonas*, the genus *Irpex*, the genus *Sporotrichum*, and the genus *Humicola* described in "Cellulase" (published by Kodansha Scientific (1987)) and "Dictionary of Cellulose" (published by Asakura Shoten (2000)). However, the cellulase of the present invention is not limited to the enzyme derived from the above-described microorganisms known in the art and also encompasses any of enzymes that decompose cellulose, including enzymes derived from microorganisms newly discovered.

Preferably, the cellulase used in the present invention has an active ratio of β-glucosidase activity to crystalline cellulose-decomposing activity (β-glucosidase activity/crystalline cellulose-decomposing activity at a temperature of 55° C.) not greater than 0.7. The activity ratio used herein is given by the ratio of the ability to decompose cellooligosaccharide (by β-glucosidase) to the ability of the cellulase to decompose cellulose (crystalline cellulose-decomposing activity). A smaller activity ratio is preferred because higher ability to decompose cellulose and lower ability to decompose oligosaccharide are attained and the productivity of oligosaccharide is improved. The activity ratio is more preferably not greater than 0.5, still preferably not greater than 0.4, particularly preferably not greater than 0.35, most preferably not greater than 0.30. Since a smaller activity ratio attains more improvement in the yield of cellooligosaccharide, the smallest activity ratio is not particularly limited and however, is not smaller than 0.01 in the light of the range of an activity ratio easily achieved.

The β-glucosidase activity used herein refers to the enzyme activity of producing glucose from cellobiose when cellobiose, a type of cellooligosaccharide, is used as a substrate, on which cellulase is in turn allowed to act in an aqueous medium. The activity is measured by the number of moles of glucose generated in 1 mL of a reaction solution for 1 minute (μmol/mL*min.) and expressed as a unit: U (unit)/mL. This β-glucosidase activity can be measured by dissolving 2% by mass of cellobiose (manufactured by Aldrich, special grade) and cellulase in 50 mM acetic acid/sodium acetate buffer at pH 4.5 and quantifying glucose concentration in the reaction solution after 1-hour reaction in a water bath at 55° C. under sealed conditions.

The crystalline cellulose-decomposing activity used herein refers to the enzyme activity of producing cellooligosaccharide such as cellobiose and cellotriose as well as glucose when crystalline cellulose is used as a substrate, on which cellulase is allowed to act in an aqueous medium. The activity is measured by the total number of moles of cellooligosaccharide and glucose generated in 1 mL of a reaction solution for 1 minute (μmol/mL*min.) and expressed as a unit: U (unit)/mL. This crystalline cellulose-decomposing activity can be measured by the above-described β-glucosidase activity measurement method, by which 5% by mass of crystalline cellulose (which is obtained by kneading and stirring Ceolus PH-101 (trade name, manufactured by Asahi Kasei Chemicals) whose moisture content has been brought to 60%, using a hook blade in an universal stirring mixer (trade name, manufactured by Sanei Manufacturing) at 126 rpm for 90 minutes) is used instead of cellobiose and enzymatically decomposed in the same way as above to quantify the whole amount of sugars decomposed and generated such as cellooligosaccharide and glucose in the reaction solution.

In the above-described various activity measurement methods, cellooligosaccharide and glucose in the reaction solution can be quantified by high performance liquid chromatography (column: Asahipak $NH_2P$-50 (trade name, manufactured by Shimadzu), high performance liquid chromatography: SCL-10A model (trade name, manufactured by Shimadzu), moving bed: acetonitrile/water=75/25 (by volume), circulation flow: 1 mL/min., sample solution: 10 μL).

Methods of obtaining cellulase having an activity ratio of β-glucosidase activity to crystalline cellulose-decomposing activity (β-glucosidase activity/crystalline cellulose-decomposing activity) that satisfies the scope of the present invention include followings:

It is preferred that a strain that produces cellulase having an activity ratio (β-glucosidase activity/crystalline cellulose-decomposing activity at a temperature of 40° C.) not greater than 0.5 should be used as the cellulase-producing fungi. Any strain can be used as long as the activity ratio satisfies the above-described range. Any of mutant strains obtained by artificial mutagenesis methods of strains (e.g., ultraviolet irradiation, X-ray irradiation, treatment with mutation inducers), naturally-occurring mutant strains, or mutant strains obtained by gene manipulation or cell fusion can be used in the present invention as long as the mutant strain produces cellulase having an activity ratio (β-glucosidase activity/crystalline cellulose-decomposing activity at a temperature of 40° C.) not greater than 0.5. This ratio (β-glucosidase activity/crystalline cellulose-decomposing activity at a temperature of 40° C.) is preferably not greater than 0.35, more preferably not greater than 0.2. Since a smaller activity ratio attains more improvement in the yield of cellooligosaccharide, the smallest activity ratio is not particularly limited and however, is not smaller than 0.01 in the light of the range of an activity ratio easily achieved.

The β-glucosidase activity and the crystalline cellulose-decomposing activity at a temperature of 40° C. are measured by a method below.

(1) Crystalline Cellulose-Decomposing Activity

After 0.4 ml of a substrate solution of 5% by mass of crystalline cellulose (which is obtained by kneading and stirring Ceolus PH-101 (trade name, manufactured by Asahi Kasei Chemicals) whose moisture content has been brought to 60%, using a hook blade in an universal stirring mixer (trade name, manufactured by Sanei Manufacturing) at 126 rpm for 90 minutes) suspended in 50 mM acetic acid-sodium acetate buffer (pH 5) is supplemented with 0.1 ml of an enzyme solution appropriately diluted, the mixture is reacted in a water bath at 40° C. for 4 hours and then heated at 95° C. for 10 minutes to terminate the reaction, followed by the quantification of glucose concentration in the reaction solution by a HPLC method. The amount of the enzyme that liberates a total of 1 μmole of glucose and cellooligosaccharide for 1 minute is defined as 1 enzyme unit (1 U).

(2) β-Glucosidase Activity

After 0.4 ml of a substrate solution of 2.5% by mass of cellobiose (manufactured by Aldrich, special grade) dissolved in 50 mM acetic acid-sodium acetate buffer (pH 5) is supplemented with 0.1 ml of an enzyme solution, the mixture is reacted in a water bath at 40° C. for 4 hours and then heated at 100° C. for 10 minutes to terminate the reaction, followed by the quantification of glucose concentration in the reaction solution by a HPLC method. The amount of the enzyme that liberates 1 μmole of glucose for 1 minute is defined as 1 enzyme unit (1 U).

In the above-described various activity measurement methods, cellooligosaccharide and glucose in the reaction solution can be quantified by the above-described high performance liquid chromatography.

Here, an example of a typical strain used includes a *Trichoderma reesei* NBRC31329 strain.

In addition, the strain where an activity ratio (β-glucosidase activity/crystalline cellulose-decomposing activity at a temperature of 40° C.) is small is obtained by, for example, a method below. A microorganism having the ability to produce cellulase is subjected, if necessary, to mutagenesis treatment known in the art such as ultraviolet irradiation or the use of a mutation inducer (e.g., nitrosoguanidine), and a strain where an activity ratio (β-glucosidase activity/crystalline cellulose-decomposing activity) is small is selected from its strains. For example, *Trichoderma reesei* NBRC31329 is used as the microorganism (parent strain) used in mutagenesis treatment and is cultured on a potato dextrose agar slant medium at 28° C. for 3 to 10 days. Generated spores are suspended at $10^5$ to $10^8$ spores/mL in saline and subjected to mutagenesis treatment with EMS (ethyl methanesulfonate) (100 to 500 μg/ml, pH 7.0, 28° C., 5 to 24 hrs). The selection of a strain where an activity ratio (β-glucosidase activity/crystalline cellulose-decomposing activity at a temperature of 40° C.) is small is achieved by collecting the spores from a suspension of the mutagenesis-treated spores by centrifugation and washing the spores, which are in turn cultured with glucose as a carbon source, followed by the measurement of enzyme activity of the resulting culture by a method known in the art. A strain of interest may be selected quantitatively by using a culture from each mutagenesis-treated strain and enzymatically decompose cellobiose or crystalline cellulose used as a substrate to quantify a reducing sugar generated, or otherwise may be selected qualitatively by using a colorimetric substrate known in the art which is enzymatically reacted with the culture.

Cellulase can be acquired from a culture supernatant liquid obtained by culturing the cellulase-producing fungi strain. The carbon source used in a medium is exemplified by cellulose powder, cellobiose, filter paper, general papers, sawdust, bran, chaff, bagasse, soybean cake, coffee grounds, starch, and lactose. Inorganic ammonium salts such as ammonium nitrate and ammonium sulfate as well as organic nitrogen-containing substances such as urea, amino acids, meat extracts, yeast extracts, polypeptone, and protein decomposition products are used as nitrogen sources. $KH_2PO_4$, $MgSO_4 \cdot 7H_2O$, $CaCl_2 \cdot 2H_2O$, $Fe_2Cl_3 \cdot 6H_2O$, $MnCl_3 \cdot 4H_2O$, $ZnSO_4 \cdot 7H_2O$, and the like are used as inorganic salts. A medium containing an organic micronutrient is optionally used. For culture, a usual aerated spinner culture apparatus is used, and the above-described medium is used and controlled around a temperature and pH that allow the growth of the producing strains. Subsequently, the strain bodies are removed from the resulting culture solution by a method known in the art such as centrifugation and filtration to obtain a supernatant liquid. This supernatant liquid can directly be used as a crude enzyme solution.

An example of a culture method for further reducing the activity ratio (β-glucosidase activity/crystalline cellulose-decomposing activity at a temperature of 40° C.) includes a method of controlling the pH of the culture solution during culture at less than 3.5 and not smaller than pH that allows the growth of the cellulase-producing fungi. Specifically, the above-described *Trichoderma reesei* NBRC31329 strain or a mutant strain thereof is cultured on potato dextrose agar slant at 25 to 35° C. for 3 to 10 days. The resulting cultures are inoculated and precultured at 28° C. for 2 to 4 days in a medium where 100 mL of a medium containing cellulose as a carbon source suspended and dissolved has been dispensed into 500-mL Erlenmeyer flasks and autoclaved. The preculture solution is inoculated into a medium where 3 L of a medium having the same composition as above has been placed in a 5-L jar fermentor and autoclaved, and is cultured at a temperature of 28° C., a stirring rate of 200 to 400 rpm, and an aeration rate of 0.3 to 1 vvm. The pH during culture is controlled at 2 to 3.5, preferably 2.5 to 3.0, with NaOH or ammonia water. Following 4- to 7-day culture, the strain bodies are removed from the culture solution by a method known in the art such as centrifugation and filtration to obtain a supernatant. This supernatant can directly be used as a crude enzyme solution.

The crude enzyme solution thus obtained may further be purified by a usual protein purification method, for example, ammonium sulfate fractionation, precipitation fractionation with a solvent, or column chromatography.

Alternatively, when the cellulase is obtained from a commercially-available enzyme, the enzyme is purified by a usual protein purification method such as ammonium sulfate fractionation, precipitation fractionation with a solvent, or column chromatography to obtain a fraction having an activity ratio (β-glucosidase activity/crystalline cellulose-decomposing activity at a temperature of 55° C.) not greater than 0.7.

Hereinafter, a process of producing cellooligosaccharide of the present invention will be described.

The process of producing cellooligosaccharide of the present invention is a process of enzymatically decomposing the natural cellulosic material of the present invention in the presence of cellulase. It is preferred that the cellulase used in the process should has an activity ratio of β-glucosidase activity to crystalline cellulose-decomposing activity (β-glucosidase activity/crystalline cellulose-decomposing activity at a temperature of 55° C.) not greater than 0.7. An aqueous solution mainly composed of the cellooligosaccharide obtained in the present invention is purified and/or dried by a method known in the art.

Any method known in the art may be used without particular limitation as a method for enzymatic decomposition. One example thereof includes a method in which the cellulosic material of the present invention as a substrate is suspended in an aqueous medium, then supplemented with the cellulase of the present invention, and heated with stirring or shaking to perform saccharification reaction.

In the above-described method, reaction conditions such as suspending and stirring procedures, the procedure and order for adding the cellulase/substrate, and their concentrations are appropriately adjusted to give cellooligosaccharide in higher yields. In this case, the pH and temperature of the reaction solution may fall within the range that does not inactivate the enzyme and in general, may be in the temperature range of 5 to 95° C. and the pH range of 1 to 11 when the reaction is performed under normal pressure. On this occasion, the pressure, temperature, and pH are also appropriately adjusted to give cellooligosaccharide in higher yields, as described above. However, in the case of using cellulase obtained with the above-described *Trichoderma reesei* NBRC31329 strain or a mutant strain thereof as cellulase-producing fungi, it is preferred that the cellulose should enzymatically decomposed in an acetate or phosphate buffer under normal pressure at a temperature of 50 to 60° C. and a pH of 3.0 to 5.5.

This enzyme reaction may be performed as both batch and continuous systems. For avoiding product inhibition by cellobiose in the enzymatic decomposition reaction, cellobiose concentration in the reaction system, which is kept within a certain range, is important in improving the productivity of cellooligosaccharide. A method for keeping cellobiose concentration in the reaction system within a certain range may be a method where generated cellobiose is extracted from the reaction system by membrane filtration such as ultrafiltration or reverse osmosis filtration; a method where a porous organic base material such as a dried plant powder (e.g., activated carbon, a bamboo, and a wood), a porous inorganic base material such as silicon dioxide, and the like, are introduced into the reaction system and cellobiose is adsorbed in them; a method where the cellulose substrate is immobilized in a column or the like, in which a reaction solution containing the cellulase is circulated; or a method where the cellulase is immobilized in a polymer or the like, in which a reaction solution containing the cellulose is circulated.

An aqueous solution mainly composed of the cellooligosaccharide obtained by the above-described enzymatic decomposition can optionally be subjected to purification treatment such as decolorization, desalting, and enzyme removal. The purification method is not particularly limited as long as the method is known in the art. However, for example, activated carbon treatment, ion-exchange resin treatment, chromatography treatment, filtration treatment such as microfiltration, ultrafiltration, and reverse osmosis filtration, and crystallization treatment may be used. These methods may be used alone, or two or more of them may be combined.

The aqueous solution mainly composed of the cellooligosaccharide, which has been purified by the above-described method can be used without further treatment and however, if necessary, may be solidified by drying. The drying method is not particularly limited as long as the method is known in the art. However, for example, spray drying, freeze drying, drum drying, thin-film drying, plate drying, flash drying, and vacuum drying may be used. These methods may be used alone, or two or more of them may be combined.

In the above-described purification and drying treatments, for example, an organic solvent in addition to water may optionally be used as a medium for cellooligosaccharide. No particular limitation is imposed on the organic solvent used in the treatment. The organic solvent is preferably any of those used at a step of producing, for example, pharmaceuticals, foods, and additives thereof and includes those classified as solvents in "Dictionary of Pharmaceutical Additives" (published by Yakuji Nippo), and "Japanese Pharmacopoeia" and "Official Method for Food Additives" (published by Hirokawa Publishing). Water and the organic solvents may be used alone, or two or more of them may be used in combination. Alternatively, after one medium is used in dispersion and then removed, the cellooligosaccharide may be dispersed again in a different medium.

The cellooligosaccharide that has undergone the above-described steps can be used in a form including, but not particularly limited to, a solid, a suspension, an emulsion, a syrup, or a solution at normal temperature. One example of the solid cellooligosaccharide includes a powder, a granule, a pellet, a molded matter, a laminate, and a solid dispersion.

Cellooligosaccharide obtainable by the process of the present invention is explained below.

The cellooligosaccharide of the present invention has a diethyl ether-soluble substance content preferably of 2000 ppm or less, more preferably of 1000 ppm or less. The diethyl ether-soluble substance content used herein refers to the content of impurities soluble in diethyl ether, such as lignin, lignin-decomposed matter in the cellulosic material, and can be measured by the quantitative procedure for diethyl ether-soluble substance defined in Crystalline Cellulose Purity Test (2) of Japanese Pharmacopoeia (the 14th revision, published by Hirokawa Publishing). Cellooligosaccharide having a diethyl ether-soluble substance content of 2000 ppm or less is preferable because it contains less impurities to show a high whiteness and can be easily purified upon using it in foods, cosmetics and pharmaceutical preparations. Particularly, when a cellooligosaccharide is used in combination with an active ingredient such as a medicament, it is preferable because it can reduce the decomposition of the active ingredient. When the cellooligosaccharide is used as a starting material for chemical conversion, it is preferable because it less likely causes side reactions and enhances chemical conversion and yield because of less impurities. The diethyl ether-soluble substance content is more preferably 1000 ppm or less, further preferably 500 ppm or less, still further preferably 300 ppm or less, most preferably 100 ppm or less. The less the diethyl ether-soluble substance content is, the more the above-mentioned effect becomes. Thus, although the lower limit thereof is not particularly restricted, the range of lignin content is 0.1 ppm or more, which can be achieved by concise procedure.

The cellooligosaccharide obtained by the present invention is not particular limited by applications and may be used as, for example, food, cosmetic, pigment, flavor, pharmaceutical active, agrochemical, feed, fertilizer, medium, and analytical reagent ingredients, an additive, an intermediate raw material, and a fermentation raw material in fields such as foods, cosmetics, pharmaceuticals, and general industrial products.

The application of the cellooligosaccharide obtained by the present invention in foods includes: gel such as jelly, pudding, and yogurt; seasonings such as mayonnaise, dressing, sauces, gravies, soup, and processed vegetable; retort foods and chilled foods such as curry, hashed meat, meat sauce, stew, and soup; processed livestock products such as hamburger, bacon, sausage, salami sausage, and hams; fish paste products such as boiled fish paste, tube-shaped fish paste cake, fish ham/sausage, and fried fish paste; processed wheat foods such as bread, wet noodle, dried noodle, macaroni, spaghetti, pasta wrapping for Chinese steamed bread, cake mix, premix, white sauce, and paste wrappings for jiao-zi and spring roll; canned and bottled foods such as curry, sauce, soup, food boiled in soy sauce, and jam; confectioneries such as candy, troche, tablet, chocolate, biscuit, cookie, rice biscuit, Japanese/western confectionary, unbaked cake, snack food, confection, and pudding; cooked and processed foods such as fried foods, croquette, jiao-zi, and Chinese steamed bread; and pastes such as vegetable paste, minced meat, fruit paste, and fish and seafood paste. Also included are milk products such as ice cream, ice milk, lact ice, whipped cream, condensed milk, butter, yogurt, cheese, and white sauce as well as processed oil and fat products such as margarine, fat spread, and shortening. In addition, the cellooligosaccharide may be used in carbonated beverages such as Coke; beverages such as carbonated fruit beverages, alcoholic fruit beverages, fruit beverages mixed with milk products, beverages with juice or pulp, and milk beverages; lacetic acid/milk beverages such as coffee, milk, soy milk, cocoa milk, fruit milk, and yogurt; and tea drinks such as boiled tea, oolong, green powdered tea, and black tea.

The cellooligosaccharide obtained in the present invention is expected to attain diverse physiological activity such as the activation of useful intestinal bacterial flora (e.g., the activation of lacetic acid bacteria and lactobacilli), reduction in blood sugar concentration and blood insulin concentration, reduction in blood cholesterol, decrease in body fat percentage, the function of promoting lipid/carbohydrate metabolism, improvement in bowel movement/stercoral odor, and anti-caries properties. Thus, in addition to the above-described applications in usual foods, the cellooligosaccharide may be used as a physiologically-active substance in applications such as functional foods, healthy foods, and diet foods.

Furthermore, because the cellooligosaccharide obtained in the present invention is highly pure, the cellooligosaccharide may be used as a raw material for chemical conversion into a variety of cellooligosaccharide derivatives.

EXAMPLES

Although the present invention will be described in accordance with Examples, the present invention is not intended to be limited to them.

Example 1

In a low-speed stirrer (30-L reactor), 2 kg of commercially-available dissolving pulp derived from a coniferous tree (average degree of polymerization: 781, diethyl ether-soluble substance content: 1.1%, average particle size: 174 μm) and 30 L of 3 N hydrochloric acid solution were placed and hydrolyzed with stirring at 105° C. for 30 minutes. The resulting acid-insoluble residue was filtered with a Nutsche and washed four times in 70 L of pure water to obtain wet cake having a solid content of 40.1% (average degree of polymerization: 220, diethyl ether-soluble substance content: 0.03% by mass, average particle size: 69.1 μm, colloidal cellulose content: 13.4% by mass, cellulose I crystals content: 85%).

A commercially-available cellulase preparation derived from *Trichoderma* (trade name: T"Amano"4) which had been dissolved in 0.2 N acetic acid-sodium acetate buffer (pH 4.5) was added to the wet cake so that the solid content and protein concentration of the wet cake were adjusted to 5% and 0.25%, respectively. The mixture (25 mL in total) thus obtained was placed in a 50-mL glass vial. This glass vial was placed in a constant-temperature shaking water bath at 48° C. and reacted at a shaking speed of 90 rpm for a fixed period of time shown in Table 1. In a fixed period of time shown in Table 1 after the initiation of reaction, 300 μL of the reaction solution remaining suspended was dispensed. After an ultrafiltration module (molecular weight cut-off: 5000) was used to remove the enzyme, the resulting solution was analyzed by high performance liquid chromatography (manufactured by Shimadzu, column: TSK-GEL AMIDO-80 (trade name, manufactured by Tosoh), moving bed: acetonitrile/water=6/4). The obtained result is shown in Table 1. The selectivity of oligosaccharide in the table is a value calculated by (cellobiose concentration+cellotriose concentration)/total sugar concentration×100(%).

Example 2

Commercially-available dissolving pulp derived from a coniferous tree (average degree of polymerization: 781, diethyl ether-soluble substance content: 1.1%, average particle size: 174 μm) was subjected to acid hydrolysis in the same way as Example 1. The resulting wet cake was made into a flock form, then placed in a flash drier at 60° C., and dried for 12 hours.

The resulting dried material was crushed with a home-use mixer, and the obtained crushed cellulose material was pulverized with an air-jet crusher (manufactured by Seishin Enterprise, trade name: Jet Mill STJ-2000 model) to obtain a cellulose powder (average degree of polymerization: 220, diethyl ether-soluble substance content: 0.03% by mass, average particle size: 16.4 μm, colloidal cellulose content: 17.5% by mass, cellulose I crystals content: 86%). This cellulose powder was used as a substrate and enzymatically decomposed in the same way as Example 1. The obtained result is shown in Table 1.

Example 2 employed the average degree of polymerization and diethyl ether-soluble substance content identical to those in Example 1, the average particle size smaller than in Example 1, and the colloidal cellulose content larger than in Example 1. As seen from Table 1, in Example 2, the reaction time required for sugar concentration to reach 10% and 20% was reduced and the selectivity of oligosaccharide was improved for each sugar concentration, as compared with Example 1, by reducing the average particle size of the substrate.

Example 3

Commercially-available dissolving pulp derived from a broadleaf tree (average degree of polymerization: 1682, diethyl ether-soluble substance content: 0.9%, average particle size: 91 μm) was subjected to acid hydrolysis in the same way as Example 1. The resulting wet cake was supplemented with pure water to make a dispersion having a cellulose concentration of 10%. The dispersion was stirred for 30 minutes with a high-shear homogenizer (manufactured by Tokushu Kika Kogyo, trade name TK Homogenizer) to obtain a cellulose dispersion (average degree of polymerization: 151, diethyl ether-soluble substance content: 0.1% by mass, average particle size: 8.7 μm, colloidal cellulose content: 55.5% by mass, cellulose I crystals content: 85%). This cellulose dispersion was used as a substrate and enzymatically decomposed in the same way as Example 1. The obtained result is shown in Table 1.

Example 3 employed smaller average degree of polymerization, higher diethyl ether-soluble substance content, smaller average particle size, and higher colloidal cellulose content, than those in Examples 1 and 2. As seen from Table 1, in Example 3, the reaction time was further reduced and the selectivity of oligosaccharide was improved for each sugar concentration, as compared with Examples 1 and 2. Although the selectivity of oligosaccharide decreased with a rise in sugar concentration in Examples 1 and 2, the selectivity of oligosaccharide did not decrease in Example 3 even by a rise in sugar concentration.

Example 4

Commercially-available dissolving pulp derived from a coniferous tree (average degree of polymerization: 781, diethyl ether-soluble substance content: 1.1% by mass, average particle size: 174 μm) was subjected to hydrolysis in the same way as Example 1 except for conditions of hydrolysis conducted with 5 N hydrochloric acid solution at hydrochloric acid concentration at 18° C. for 12 hours. As with Example 1, the resulting acid-insoluble residue washed and filtrated to obtain wet cake (average degree of polymerization: 690, diethyl ether-soluble substance content: 0.7%, average particle size: 49.8 μm). This wet cake was made into a water dispersion having a cellulose concentration of 10%. The water dispersion was subjected to consolidation/grinding treatment with a super-performance dispersing/wet-pulverizing machine (manufactured by Ashizawa, trade name: Pearl Mill RL, with φ2 mm alumina beads, filling rate: 80%) to obtain a cellulose particulate dispersion (average degree of polymerization: 690, diethyl ether-soluble substance content: 0.7% by mass, average particle size: 7.1 μm, colloidal cellulose content: 87.5% by mass, cellulose I crystals content: 77%). This cellulose particulate dispersion was used as a substrate and enzymatically decomposed in the same way as Example 1. The obtained result is shown in Table 1.

Example 4 employed higher average degree of polymerization and diethyl ether-soluble substance content, smaller average particle size, and higher colloidal cellulose content, than those in Examples 1, 2, and 3. As seen from Table 1, in Example 4, the selectivity of oligosaccharide was equal to that in Example 3 and however, the reaction time was improved as compared with Examples 3. Moreover, the selectivity of oligosaccharide hardly decreased in Example 4 even by a rise in sugar concentration.

Example 5

Hydrolysis was conducted in the same way as in Example 1 except that commercially-available pulp derived from cotton linter (average degree of polymerization: 1853) was used and the hydrolysis was conducted in 5 N aqueous hydrochloric acid solution at 130° C. for 12 hours, to obtain wet cake (average degree of polymerization: 49). This wet cake was made into a water dispersion having a cellulose concentration of 10%. The water dispersion was subjected to consolidation/grinding treatment with a super-performance dispersing/wet-pulverizing machine (manufactured by Ashizawa, trade name: Pearl Mill RL, with φ2 mm alumina beads, filling rate: 80%) to obtain a cellulose particulate dispersion (average degree of polymerization: 49, diethyl ether-soluble substance content: 0.9% by mass, average particle size: 10.3 μm, colloidal cellulose content: 94.1% by mass, cellulose I crystals content: 75%). This cellulose particulate dispersion was used as a substrate and enzymatically decomposed in the same way as in Example 1 except for changing the enzyme to CELLULASENAGASE (manufactured by Nagase & Co., Ltd., trade name) derived from *Aspergillus niger*. The obtained result is shown in Table 1.

Example 5 employed lower average degree of polymerization, higher diethyl ether-soluble substance content and larger average particle size but higher colloidal cellulose content, than Example 4. As seen from Table 1, in Example 5, the reaction time was decreased by half and the selectivity of oligosaccharide increased than in Example 4.

Comparative Example 1

The commercially-available coniferous tree-derived dissolving pulp used in Example 1 was added to 3 N hydrochloric acid solution to make a dispersion having a cellulose concentration of 10%. The dispersion was stirred at normal temperature for 60 minutes with a high-shear homogenizer (manufactured by Tokushu Kika Kogyo, trade name TK Homogenizer) to obtain a cellulose dispersion (average degree of polymerization: 723, diethyl ether-soluble substance content: 0.9% by mass, average particle size: 49.3 μm, colloidal cellulose content: 10.2% by mass, cellulose I crystals content: 85%). This cellulose dispersion without undergoing acid hydrolysis was used as a substrate and enzymatically decomposed in the same way as Example 1. The obtained result is shown in Table 1.

Comparative Example 1 employed the average particle size and diethyl ether-soluble substance content falling within the scope of the present invention and the average degree of polymerization exceeding the scope. As seen from Table 1, in Comparative Example 1, the reaction time required for sugar concentration to reach 10% and 20% was extended and the enzymatic decomposition was slowed, as compared with each Example. In addition, the selectivity of oligosaccharide for any sugar concentration fell short of the level of each Example.

Comparative Example 2

The wet cake obtained by the procedures in Example 4 was made into a water dispersion having a cellulose concentration of 10%. The water dispersion was subjected to wet fractionation using a sieve having a mesh size of 45 μm. A solid content (average degree of polymerization: 690, diethyl ether-soluble substance content: 0.7% by mass, average particle size: 107.3 μm, colloidal cellulose content: 5.2% by mass, cellulose I crystals content: 85%) remaining on the sieve was used as a substrate and enzymatically decomposed in the same way as Example 1. The obtained result is shown in Table 1.

Comparative Example 2 employed the average degree of polymerization and diethyl ether-soluble substance content falling within the scope of the present invention and the average particle size exceeding the scope. As seen from Table 1, in Comparative Example 2, the reaction time was slowed as compared with each Example, and the selectivity of oligosaccharide fell short of the level of each Example.

Comparative Example 3

Commercially-available unbleached kraft pulp derived from a coniferous tree (average degree of polymerization: 1670, diethyl ether-soluble substance content: 12% by mass, average particle size: 154 μm) was subjected to hydrolysis in the same was as Example 1 except for conditions of hydrolysis conducted with 4 N hydrochloric acid solution at hydrochloric acid concentration at 35° C. for 18 hours. As with Example 1, the resulting acid-insoluble residue washed and filtrated to obtain wet cake (average degree of polymerization: 490, diethyl ether-soluble substance content: 4.4% by mass, average particle size: 48.7 μm, colloidal cellulose content: 12.8% by mass, cellulose I crystals content: 86%).

This wet cake was used and enzymatically decomposed in the same way as Example 1. The obtained result is shown in Table 1.

Comparative Example 3 employed the average degree of polymerization and average particle size falling within the scope of the present invention and the diethyl ether-soluble substance content exceeding the scope. As seen from Table 1, in Comparative Example 3, the yield of cellooligosaccharide was slightly improved as compared with Comparative Examples 1 and 2 and however, both of the reaction time and the selectivity of oligosaccharide fell short of the levels of Examples.

TABLE 1

Fundamental physical property of cellulose substrate

| | Average degree of polymerization (−) | Average particle size (μm) | Colloidal component content (% by mass) | Diethyl ether-soluble substance content (% by mass) | Enzymatic decomposition data | | |
|---|---|---|---|---|---|---|---|
| | | | | | Total sugar concentration (mg/mL) | Reaction time (hr) | Selectivity of oligo-saccharide (%) |
| Example 1 | 220 | 69.1 | 13.4 | 0.03 | 10 | 5 | 54.0 |
| | | | | | 20 | 19 | 13.0 |
| Example 2 | 220 | 16.4 | 17.5 | 0.03 | 10 | 4 | 61.0 |
| | | | | | 20 | 17 | 15.0 |
| Example 3 | 151 | 8.7 | 55.5 | 0.1 | 10 | 1.5 | 54.0 |
| | | | | | 20 | 5 | 55.5 |
| Example 4 | 690 | 7.1 | 87.5 | 0.7 | 10 | 1 | 57.0 |
| | | | | | 20 | 4 | 52.0 |
| Example 5 | 49 | 10.3 | 94.1 | 0.9 | 10 | 0.6 | 61.0 |
| | | | | | 20 | 2 | 60.5 |
| Comparative Example 1 | 723 | 49.3 | 10.2 | 0.9 | 10 | 10 | 33.0 |
| | | | | | 20 | 36 | 7.5 |
| Comparative Example 2 | 690 | 107.3 | 5.2 | 0.7 | 10 | 8 | 15.0 |
| | | | | | 20 | 24 | 8.5 |
| Comparative Example 3 | 490 | 48.7 | 12.8 | 4.4 | 10 | 12 | 37.2 |
| | | | | | 20 | 44 | 10.5 |

Production Example 1

After *Trichoderma reesei* NBRC31329 was inoculated into a potato dextrose medium (manufactured by Difco) and cultured at 37° C. for 7 days, one loopful of spores taken from the surface of the medium was inoculated and precultured at 28° C. for 3 days in a medium where 1 g of polypeptone, 0.5 g of a yeast extract, 2 g of monopotassium phosphate, 1.5 g of ammonium sulfate, 0.3 g of magnesium sulfate, 0.3 g of calcium chloride, 1 mL of a trace element (which had been obtained by dissolving 6 mg of boric acid, 26 mg of ammonium molybdate tetrahydrate, 100 mg of iron (III) chloride hexahydrate, 40 mg of copper sulfate pentahydrate, 8 mg of manganese sulfate tetrahydrate, and 200 mg of zinc sulfate heptahydrate in a total of 100 mL of purified water), 1 mL of Adecanol LG-109, and 10 g of crystalline cellulose (manufactured by Asahi Kasei Chemicals, trade name: PH-101) had been suspended and dissolved in a total of 1 L of purified water, whose 100 mL had in turn been dispensed to 500-mL Erlenmeyer flasks and autoclaved. Further, 10 mL of the preculture solution was inoculated into a 5-L jar fermentor in which 1 L of a medium having the same composition as above had been placed, and was cultured at a temperature of 28° C., a stirring rate of 400 rpm, and an aeration rate of 0.5 vvm. The pH during culture was controlled at 3 with NaOH. Following 7-day culture, the resulting solution was centrifuged. The strain bodies were removed from the obtained supernatant with a microfiltration membrane having a mesh size of 0.46 μm. The filtrate was condensed tenfold by volume with an ultrafiltration membrane having a molecular weight cut-off of 13000 (manufactured by Asahi Kasei Chemicals, trade name: Microza Pencil Module ACP-0013) to obtain a crude enzyme.

Table 2 shows the result of this crude enzyme measured for an activity ratio (β-glucosidase activity/crystalline cellulose-decomposing activity at a temperature of 55° C.).

Production Example 2

After *Trichoderma reesei* NBRC31329 was inoculated into a potato dextrose medium (manufactured by Difco) and cultured at 37° C. for 7 days, one loopful of spores taken from the surface of the medium was inoculated and cultured at 28° C. for 3 days in a medium where 1 g of polypeptone, 0.5 g of a yeast extract, 2 g of monopotassium phosphate, 1.5 g of ammonium sulfate, 0.3 g of magnesium sulfate, 0.3 g of calcium chloride, 1 mL of a trace element (which had been obtained by dissolving 6 mg of boric acid, 26 mg of ammonium molybdate tetrahydrate, 100 mg of iron (III) chloride hexahydrate, 40 mg of copper sulfate pentahydrate, 8 mg of manganese sulfate tetrahydrate, and 200 mg of zinc sulfate heptahydrate in a total of 100 mL of purified water), 1 mL of Adecanol LG-109, and 10 g of crystalline cellulose (manufactured by Asahi Kasei Chemicals, trade name: PH-101) had been suspended and dissolved in a total of 1 L of purified water, whose 100 mL had in turn been dispensed to 500-mL Erlenmeyer flasks and autoclaved. Further, 10 mL of the preculture solution was inoculated into a 5-L jar fermentor in which 1 L of a medium having the same composition as above had been placed, and was cultured at a temperature of 28° C., a stirring rate of 400 rpm, and an aeration rate of 0.5 vvm. The pH during culture was controlled at 4 with NaOH. Following 7-day culture, the resulting solution was centrifuged. The strain bodies were removed from the obtained supernatant with a microfiltration membrane having a mesh size of 0.46 μm. The filtrate was condensed tenfold by volume with an ultrafiltration membrane having a molecular weight cut-off of 13000 (manufactured by Asahi Kasei Chemicals, trade name: Microza Pencil Module ACP-0013) to obtain a crude enzyme.

Table 2 shows the result of this crude enzyme measured for an activity ratio (β-glucosidase activity/crystalline cellulose-decomposing activity at a temperature of 55° C.).

Production Example 3

Commercially-available cellulase (manufactured by Godo Shusei, trade name: GODO-TCD) was dissolved in 50 mM acetic acid-sodium acetate buffer (pH 4.8) to bring the concentration of the cellulase to 500 mg/mL. The mixture was introduced into an anion-exchange column (manufactured by Amersham, trade name: DEAE-Sepharose FF). Fractionated samples were obtained from the commercially-available enzyme by a linear gradient method by which 50 mM acetic acid-sodium acetate buffer (pH 4.8) and 1 mole % sodium chloride dissolved in 50 mM acetic acid-sodium acetate buffer (pH 4.8) were circulated in the column. All of the obtained fractions were measured for β-glucosidase activity and crystalline cellulose-decomposing activity, and fractions having an activity ratio (β-glucosidase activity/crystalline cellulose-decomposing activity at a temperature of 55° C.) not greater than 0.5 were combined. The obtained cellobiose fractions were condensed fivefold by volume with an ultra-filtration module having a molecular weight cut-off of 10000 (manufactured by Millipore, trade name: Amicon Ultra-15 Centrifugal Filter) to obtain a purified enzyme (protein concentration in the purified enzyme: 15.4 mg/mL).

Table 2 shows the result of this purified enzyme measured for an activity ratio (β-glucosidase activity/crystalline cellulose-decomposing activity at a temperature of 55° C.).

Example 6

In a low-speed stirrer (30-L reactor), 2 kg of Commercially-available dissolving pulp derived from a coniferous tree (average degree of polymerization: 781, diethyl ether-soluble substance content: 1.1%, average particle size: 174 μm) was placed and subjected to hydrolysis under conditions of hydrolysis conducted with 3 N hydrochloric acid solution at 110° C. for 30 minutes. The resulting acid-insoluble residue was washed and filtered to obtain wet cake. The obtained wet cake was made into a flock form and aerated/dried in an oven at 60° C. for 12 hours. The resulting dried material was supplemented with purified water to bring its moisture content to 60%, and grinded with a mixer (manufactured by Sanei Manufacturing, trade name: universal stirring mixer, with a hook blade at 126 rpm for 90 minutes) to obtain ground cellulose (average degree of polymerization: 220, average particle size: 9.1 μm, colloidal cellulose component content: 66.1% by mass, diethyl ether-soluble substance content: 0.03% by mass, cellulose I crystals content: 78%).

Then, 5% by mass of this ground cellulose was suspended and dissolved in 50 mM acetic acid-sodium acetate buffer (pH 4.8) of the crude enzyme obtained in Production Example 1. The mixture (25 mL in total) thus obtained was placed in a glass vial. This glass vial was placed in a constant-temperature shaking water bath at 55° C. and reacted at a shaking speed of 90 rpm. In a fixed period of time after the initiation of reaction, 300 μL of the reaction solution remaining suspended was dispensed. After an ultrafiltration module (molecular weight cut-off: 10000) was used to remove the enzyme and undecomposed cellulose, the resulting solution was analyzed for sugar concentration by high performance liquid chromatography. The obtained result is shown in Table 2.

Cellooligosaccharide and glucose in the reaction solution were quantified by high performance liquid chromatography (column: Asahipak $NH_2$P-50 (trade name, manufactured by Shimadzu), high performance liquid chromatography: SCL-10A model (trade name, manufactured by Shimadzu), moving bed: acetonitrile/water=75/25 (by volume), circulation flow: 1 mL/min., sample solution: 10 μL).

Reaction time in the table is reaction time required for the ratio of the total amount of sugars (cellooligosaccharide and glucose) generated to the amount of cellulose used to reach 20% by mass. The selectivity of oligosaccharide is represented by a value calculated by (cellobiose concentration+ cellotriose concentration)/total sugar concentration×100(%).

Example 7

Commercially-available dissolving pulp derived from a coniferous tree (average degree of polymerization: 781, diethyl ether-soluble substance content: 1.1%, average particle size: 174 μm) was subjected to hydrolysis in the same way as Example 1 except for conditions of hydrolysis conducted with 5 N hydrochloric acid solution at hydrochloric acid concentration at 18° C. for 12 hours. As with Example 1, the resulting acid-insoluble residue washed and filtrated to obtain wet cake (average degree of polymerization: 690, diethyl ether-soluble substance content: 0.7% by mass, average particle size: 49.8 μm). This wet cake was made into a water dispersion having a cellulose concentration of 10%. The water dispersion was subjected to consolidation/grinding treatment with a super-performance dispersing/wet-pulverizing machine (manufactured by Ashizawa, trade name: Pearl Mill RL, with φ2 mm alumina beads, filling rate: 80%) to obtain a cellulose particulate dispersion (average degree of polymerization: 690, diethyl ether-soluble substance content: 0.7% by mass, average particle size: 7.1 μm, colloidal component content: 87.5% by mass, cellulose I crystals content: 77%). Moreover, the obtained wet cake was enzymatically decomposed in the same way as Example 6. The obtained result is shown in Table 2.

In Example 7, the cellulose having smaller average particle size and higher colloidal component content than those in Example 6 was enzymatically decomposed. The reaction time was reduced and the selectivity of oligosaccharide was improved, as compared with Example 6.

Example 8

The cellulose wet cake obtained in Example 6 was used and enzymatically decomposed with the purified enzyme obtained in Production Example 3 in the same way as Example 1. The obtained result is shown in Table 2.

Example 8 employed the enzyme having an activity ratio (β-glucosidase activity/crystalline cellulose-decomposing activity) smaller than that in Example 6. Although the reaction time was extended by changing the enzyme, the selectivity was improved.

Example 9

Commercially-available dissolving pulp derived from a coniferous tree (average degree of polymerization: 781, diethyl ether-soluble substance content: 1.1% by mass, average particle size: 174 μm) was hydrolyzed with stirring at 105° C. for 30 minutes. The resulting acid-insoluble residue was filtered with a Nutsche and washed four times in 70 L of pure water to obtain wet cake having a solid content of 40.1% (average degree of polymerization: 220, average particle size: 69.1 μm, colloidal component content: 13.4% by mass, diethyl ether-soluble substance content: 0.03% by mass, cellulose I crystals content: 85%). This cellulose wet cake was used and enzymatically decomposed with the purified enzyme obtained in Production Example 3 in the same way as Example 6. The obtained result is shown in Table 2.

Example 9 employed the enzyme having an activity ratio (β-glucosidase activity/crystalline cellulose-decomposing activity) smaller than that in Example 6 as well as the cellulose having larger average particle size and lower colloidal component content than those in Example 6. Although the reaction time was extended by changing the enzyme and the substrate, the selectivity was improved.

Example 10

The cellulose wet cake obtained in Example 6 was used and enzymatically decomposed with the enzyme obtained in Production Example 2 in the same way as Example 6. The obtained result is shown in Table 2.

Example 10 employed the enzyme having an activity ratio (β-glucosidase activity/crystalline cellulose-decomposing activity) larger than that in Example 6. Although the reaction time was equal to that in Example 6 by changing the enzyme, the selectivity was reduced.

Comparative Example 4

The commercially-available pulp used in Examples 6 to 9 (average degree of polymerization: 781) was used without hydrolysis. The pulp was supplemented with pure water (solid content: 40% by mass) and subjected to grinding treatment in the same way as Example 6 to obtain wet cake (average degree of polymerization: 781, average particle size: 49.3 μm, colloidal cellulose component content: 10.2% by mass, diethyl ether-soluble substance content: 0.9% by mass, cellulose I crystals content: 85%). This wet cake was used and enzymatically decomposed in the same way as Example 6. The obtained result is shown in Table 2.

Comparative Example 4 employed the cellulose having the average degree of polymerization exceeding the scope of the present invention and the average particle size and colloidal cellulose component content falling within the scope of the present invention. The reaction time was extended and the selectivity of cellooligosaccharide was reduced as compared with each Example.

Comparative Example 5

The wet cake obtained by the procedures in Example 6 was made into a water dispersion having a cellulose concentration of 10%. The water dispersion was subjected to wet fractionation using a sieve having a mesh size of 45 μm. A solid content (average degree of polymerization: 220, average particle size: 103.4 μm, colloidal component content: 9.7% by mass, diethyl ether-soluble substance content: 0.03% by mass, cellulose I crystals content: 85%) remaining on the sieve was used as a substrate and enzymatically decomposed in the same way as Example 6. The obtained result is shown in Table 2.

Comparative Example 5 employed the average degree of polymerization and diethyl ether-soluble substance content falling within the scope of the present invention as well as the average particle size exceeding the scope and the colloidal component content smaller than the scope. In Comparative Example 5, the reaction time was slowed as compared with each Example, and the selectivity of cellooligosaccharide fell short of the level of each Example.

TABLE 2

| | Physical property value of cellulosic material | | | | Physical property value of cellulase | | | Result of enzymatic decomposition | |
| --- | --- | --- | --- | --- | --- | --- | --- | --- | --- |
| | Average degree of polymerization (−) | Average particle size (μm) | Colloidal cellulose component content (% by mass) | Diethyl ether-soluble substance content (% by mass) | β-glucosidase activity: A (U/ml) | Crystalline cellulose-decomposing activity: B (U/ml) | Activity ratio: A/B at 55° C. | Reaction time (hr) | Selectivity of oligo-saccharide (%) |
| Example 6 | 220 | 9.1 | 66.1 | 0.03 | 0.17 | 0.54 | 0.31 | 5 | 67.6 |
| Example 7 | 690 | 7.1 | 87.5 | 0.7 | 0.17 | 0.54 | 0.31 | 4 | 75.7 |
| Example 8 | 220 | 9.1 | 66.1 | 0.03 | 0.10 | 0.58 | 0.17 | 8 | 83.4 |
| Example 9 | 220 | 69.1 | 13.4 | 0.03 | 0.10 | 0.58 | 0.17 | 24 | 72.6 |
| Example 10 | 220 | 9.1 | 66.1 | 0.03 | 0.22 | 0.51 | 0.43 | 5 | 59.4 |
| Comparative Example 4 | 781 | 49.3 | 10.2 | 0.9 | 0.17 | 0.54 | 0.31 | 39 | 50.4 |
| Comparative Example 5 | 220 | 103.4 | 9.7 | 0.03 | 0.17 | 0.54 | 0.31 | 30 | 66.3 |

Example 11

*Trichoderma reesei* NBRC31329 was cultured on a potato dextrose agar slant medium at 28° C. for 7 days. Generated spores were suspended at $10^6$ spores/mL in 2 ml of 100 mM calcium phosphate buffer (pH 7) and supplemented with 24 μl of EMS (ethyl methanesulfonate). The mixture was shaken at 28° C. for 16 hours to apply mutagenesis treatment to the mixture. The spores were collected from the spore suspension by centrifugation, then well washed in 100 mM calcium phosphate buffer (pH 7), and diluted to attain 100 to 300 spores per plate. The diluent was cultured at 28° C. for 5 days in a medium where 1 g of glucose, 1 g of a yeast extract, 2 g of $(NH_4)_2SO_4$, 4 g of $KH_2PO_4$, 2 g of $Na_2HPO_4$, 200 mg of $MgSO_4.7H_2O$, 1 mg of $CaCl_2.2H_2O$, TritonX-100, 1 mL of a trace element (which had been obtained by dissolving 6 mg of boric acid, 26 mg of ammonium molybdate tetrahydrate, 100 mg of iron (III) chloride hexahydrate, 40 mg of copper sulfate pentahydrate, 8 mg of manganese sulfate tetrahydrate, and 200 mg of zinc sulfate heptahydrate in a total of 100 mL of purified water), and 20 g of agar had been dissolved or suspended in 1 L of purified water, then autoclaved, and sterilized by filtration with a membrane filter. The resulting culture solution was measured for β-glucosidase activity and crystalline cellulose-decomposing activity to select a mutant strain *Trichoderma reesei* GL-1. This mutant strain has been deposited at International Patent Organism Depositary National Institute of Advanced Industrial Science and Technology (AIST Tsukuba Central 6, 1-1, Higashi 1-chome, Tsukuba-shi, Ibaraki-ken 305-8566 Japan) under the Budapest Treaty since Apr. 15, 2005 and received Accession No. FERM BP-10323.

Example 12

Each of *Trichoderma reesei* NBRC31329 and the mutant GL-1 strain obtained in Example 11 was cultured on a potato dextrose agar slant medium at 25° C. for 7 days to sufficiently form spores. One loopful of the spores was inoculated and cultured with stirring at 28° C. for 5 days in a medium where 1.0 g of polypeptone, 0.5 g of a yeast extract, 2.0 g of $KH_2PO_4$, 1.5 g of $(NH_4)_2SO_4$, 0.3 g of $MgSO_4.7H_2O$, 0.3 g of $CaCl_2.2H_2O$, 1.0 ml of Tween 80 (manufactured by Nacalai Tesque), 1.0 ml of a trace element solution (a solution obtained by dissolving and suspending 6 mg of $H_3BO_4$, 26 mg of $(NH_4)6Mo_7O_{24}.4H_2O$, 100 mg of $FeCl_3.6H_2O$, 40 mg of $CuSO_4.5H_2O$, 8 mg of $MnSO_4.4H_2O$, and 200 mg of $ZnSO_4.7H_2O$ in 100 ml of water), and 7.5 g of tartaric acid had been dissolved and suspended in 1 L of water followed by the adjustment of pH to 4.0, whose 100 mL had been dispensed to 500-mL Erlenmeyer flasks, then supplemented with 1 g of crystalline cellulose (manufactured by Asahi Kasei Chemicals, trade name: PH-101), and autoclaved. On the five days, the culture solution was centrifuged. The resulting supernatant was measured for cellulase activity and β-glucosidase activity at a temperature of 40° C. The result is shown in Table 3.

Example 13

*Trichoderma reesei* NBRC31329 was inoculated into a potato dextrose medium (manufactured by Difco) and cultured at 37° C. for 7 days. One loopful of spores taken from the surface of the medium were inoculated and precultured at 28° C. for 3 days in a medium where 1 g of polypeptone, 0.5 g of a yeast extract, 2 g of monopotassium phosphate, 1.5 g of ammonium sulfate, 0.3 g of magnesium sulfate, 0.3 g of calcium chloride, 1 mL of a trace element (which had been obtained by dissolving 6 mg of boric acid, 26 mg of ammonium molybdate tetrahydrate, 100 mg of iron (III) chloride hexahydrate, 40 mg of copper sulfate pentahydrate, 8 mg of manganese sulfate tetrahydrate, and 200 mg of zinc sulfate heptahydrate in a total of 100 mL of purified water), and 1 mL of Adecanol LG-109 had been suspended and dissolved in a total of 1 L of purified water, whose 100 mL had in turn been dispensed to 500-mL Erlenmeyer flasks, each of which had been supplemented with 1 g of crystalline cellulose (manufactured by Asahi Kasei Chemicals, trade name: PH-101) and autoclaved. Further, 30 mL of the preculture solution was inoculated into a 5-L jar fermentor in which 3 L of a medium having the same composition as above had been placed, and was cultured at a temperature of 28° C., a stirring rate of 400 rpm, and an aeration rate of 0.5 vvm. The lowest pH during culture was controlled at 3.0 with a NaOH solution. Following 5-day culture, the resulting solution was centrifuged to obtain a supernatant as a crude enzyme. The obtained enzyme solution was measured for crystalline cellulose-decomposing activity and β-glucosidase activity by the above-described method. Temporal changes in pH during culture are shown FIG. 1, and the result of activity measurement is shown in Table 4.

Example 14

When *Trichoderma reesei* NBRC31329 was cultured in the same way as Example 13, the lowest pH during culture was controlled at 2.5 with NaOH to obtain a crude enzyme solution. The obtained enzyme solution was measured for crystalline cellulose-decomposing activity and β-glucosidase activity by the above-described method. Temporal changes in pH during culture are shown FIG. 1, and the result of activity measurement is shown in Table 4.

Comparative Example 6

When *Trichoderma reesei* NBRC31329 was cultured in the same way as Example 13, the lowest pH during culture was controlled at 3.5 or 4 or 5 with NaOH to obtain a crude enzyme solution. The obtained enzyme solution was measured for crystalline cellulose-decomposing activity and β-glucosidase activity by the above-described method. Temporal changes in pH during culture are shown FIG. 1, and the result of activity measurement is shown in Table 4.

Example 15

Figure 2:
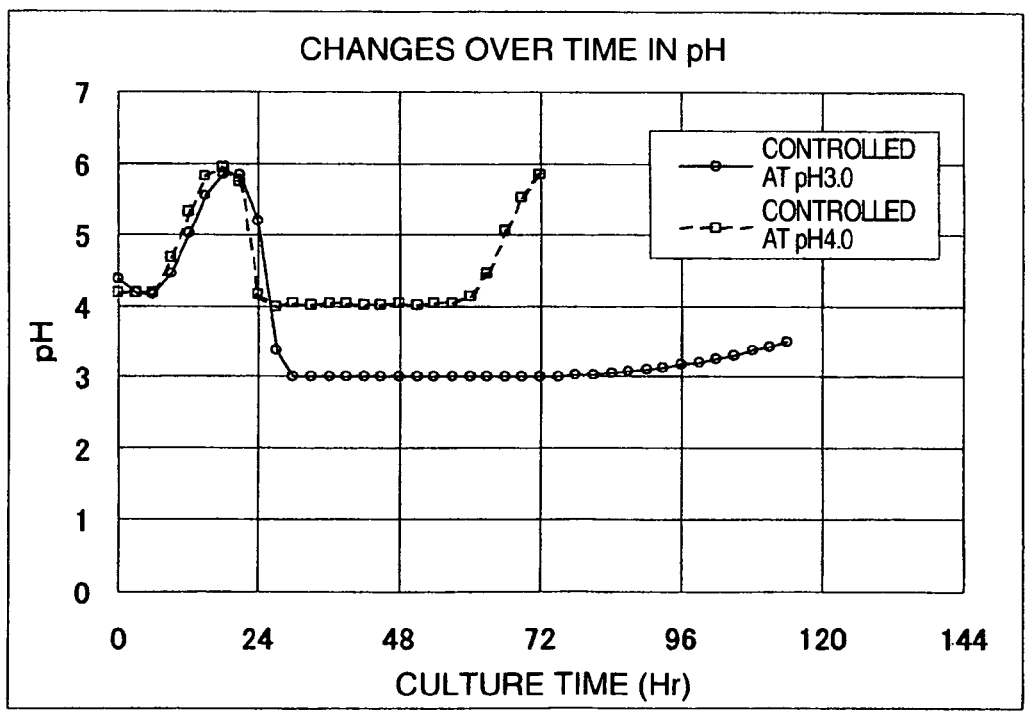
FIG. 2 is a graph showing changes over time in pH during culture in Example 15.

The GL-1 strain obtained in Example 11 was cultured in the same way as Example 13. When the strain was cultured, the lowest pH during culture was controlled at 3 or 4 with NaOH to obtain a crude enzyme solution. Temporal changes in pH during culture are shown FIG. 2.

Example 16

Figure 3:
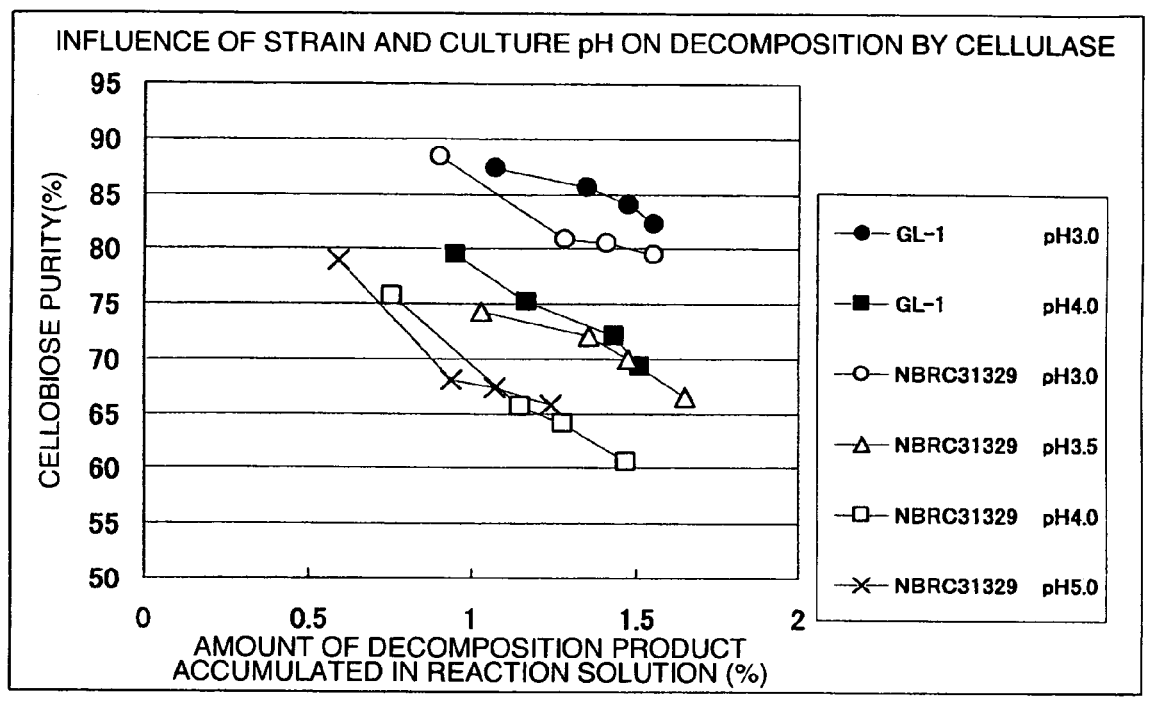
FIG. 3 is a graph showing a change in the concentration of products from crystalline cellulose decomposition in Example 16 and Comparative Example 7. In the drawing, the amount of the decomposition product accumulated (%) in a reaction solution is expressed as the total concentration of glucose and cellooligosaccharide in the reaction solution, while cellobiose purity is expressed as the ratio (percentage) of cellooligosaccharide to the amount of the decomposition product accumulated in the reaction solution. The cellobiose purity was improved for the amount of the decomposition product accumulated by using a mutant strain and reducing pH in a culture solution.

To 8 ml of 5% by mass of crystalline cellulose (which had been obtained by kneading and stirring Ceolus PH-101 (trade name, manufactured by Asahi Kasei Chemicals) whose moisture content had been brought to 60%, using a hook blade in an universal stirring mixer (trade name, manufactured by Sanei Manufacturing) at 126 rpm for 90 minutes), 2 mL of each of the cellulase crude enzyme solutions obtained in Examples 13 and 15 was added, and hydrolysis was performed under stirring conditions at 55° C. After 2-hr, 4-hr, 6-hr, and 8-hr reactions, the mixtures were heated at 95° C. for 15 minutes to terminate enzyme reaction. Supernatant liquids were obtained by centrifugation and measured for cellooligosaccharide and glucose concentrations by the above-described HPLC method. The result is shown in FIG. 3.

Comparative Example 7

When crystalline cellulose was enzymatically decomposed in the same way as Example 16, the cellulase obtained in Comparative Example 6 was used as a crude enzyme solution. The result is shown in FIG. 3.

TABLE 3

| Strain | Crystalline cellulose-decomposing activity (A) (U/ml) | β-glucosidase activity (B) (U/ml) | (B)/(A) |
|---|---|---|---|
| NBRC31329 | 0.50 | 0.23 | 0.46 |
| GL-1 | 0.58 | 0.20 | 0.34 |

TABLE 4

| Culture pH | Culture time (hr) | Crystalline cellulose-decomposing activity (A) (U/ml) | β-glucosidase activity (B) (U/ml) | (B)/(A) |
|---|---|---|---|---|
| 2.5 | 90 | 0.402 | 0.052 | 0.13 |
| 3 | 65 | 0.501 | 0.069 | 0.14 |
| 3.5 | 65 | 0.571 | 0.214 | 0.37 |
| 4 | 65 | 0.358 | 0.145 | 0.40 |
| 5 | 65 | 0.272 | 0.102 | 0.38 |

Example 17

Commercially-available crystalline cellulose (manufactured by Asahi Kasei Chemicals, trade name: PH-101) was made into a water dispersion having 10% by mass of a solid content and subjected to wet grinding with a bead mill (manufactured by Ashizawa Finetech, trade name: Pearl Mill RL5, vessel size: 5 L, grinding medium: φ1 mm zirconia beads, revolution speed: 1800 rpm, retention time in the vessel: 70 minutes). Then, 100 ml of the obtained ground cellulose water dispersion (average degree of polymerization: 220, average particle size: 0.7 μm, colloidal cellulose content: 54% by mass, diethyl ether-soluble substance content: 0.03% by mass, cellulose I crystals content: 75%) was supplemented with 200 mL of a crude enzyme solution obtained by condensing (fivefold by volume) the supernatant cultured at pH 3 in Example 15 by ultrafiltration (molecular weight cut-off: 13000). Its total volume was adjusted to 500 mL by the addition of 50 mM acetic acid/sodium acetate buffer (pH 4.5). The mixture was placed in a 1-L glass separable flask and reacted in a warm bath at 55° C. with internal stirring with 3-1 Motor (trade name). In two hours after the initiation of reaction, 300 μL of the reaction solution remaining suspended was dispensed. After an ultrafiltration module (molecular weight cut-off: 10000) was used to remove the enzyme and undecomposed cellulose, the resulting solution was analyzed for sugar concentration by high performance liquid chromatography to quantify a cellulose residue present in the reaction solution. From the result, in the reaction time of 2 hours, the decomposition rate of cellulose was 82%, and the selectivity of oligosaccharide was 81%.

Example 18

The ground cellulose water dispersion obtained in Example 17 was placed in the same flask as Example 17 and reacted under the same conditions as Example 17 using a reaction bath in which a polyacrylonitrile-made hollow ultrafiltration module having a molecular weight cut-off of 13000 (manufactured by Asahi Kasei Chemicals, trade name: Microza ACP-0013) was loaded. The reaction was conducted for 2 hours while the reaction solution was circulated in the ultrafiltration module at 0.1 MPa and a circulating flow rate of 4 L per hour. The transmitted liquid obtained by ultrafiltration was measured for sugar concentration therein to quantify a cellulose residue present in the reaction solution.

From the result, the decomposition rate of cellulose was 95% by mass, and the selectivity of oligosaccharide was 85%.

Example 19

Enzymatic decomposition was conducted using the same apparatus as Example 18 except that the cellulose concentration in the reaction solution was set to 2.5% by mass. During enzymatic decomposition, the decomposition rate of cellulose was measured by the analysis of the transmitted liquid. The reaction was conducted for 24 hours while the ground cellulose water dispersion was added so that the cellulose concentration in the reaction solution was constantly maintained at 2.5% by mass. The transmitted liquid was measured for sugar concentration therein in the same way as Example 18 to quantify a cellulose residue present in the reaction solution.

From the result, the decomposition rate of cellulose was 98% by mass, and the selectivity of oligosaccharide was 92%.

Example 20

The aqueous cellooligosaccharide solution obtained in Example 19 was subjected to removal of acetic acid through an ion-exchange resin (manufactured by Mitsubishi Chemical Corporation, trade name, DIAION WA30 and SK1B), then dried at 60° C. for 8 hours and crushed in a mortar to obtain cellooligosaccharide powder. This powder was measured for diethyl ether-soluble substance content by the quantitative procedure for diethyl ether-soluble substance defined in Crystalline Cellulose Purity Test (2) of Japanese Pharmacopoeia (the 14th revision, published by Hirokawa Publishing). The obtained diethyl ether-soluble substance content was 200 ppm.

Comparative Example 8

Commercially-available unbleached dissolving pulp (derived from Spuruce, average degree of polymerization: 1680, average particle size: 128 μm, colloidal cellulose content: 4% by mass, diethyl ether-soluble substance content: 1.5% by mass, cellulose I crystals content: 85%) was crushed with a home-use mixer. To the obtained crushed cellulose as a substrate, an acetic acid buffer of pH 5.5 was added to make an aqueous dispersion with 2% by mass of cellulose. In the above aqueous cellulose dispersion, commercially-available cellulase (manufactured by Godo Shusei, trade name: GODO-TCD) was dissolved in a concentration of 0.1% by mass based on the aqueous dispersion and allowed to conduct enzymatical decomposition at pH 5.0 for 24 hours in the same way as in Example 17. From the result, the decomposition rate of cellulose was 29% by mass, and the selectivity of oligosaccharide was 55%. This aqueous cellooligosaccharide solution was pulverized and measured for diethyl ether-soluble substance content in the same way as in Example 20. The diethyl ether-soluble substance content was 3200 ppm.

INDUSTRIAL APPLICABILITY

Cellooligosaccharide obtained by the method of the present invention can preferably be utilized not only as a raw material for usual foods but also as a raw material for functional foods, a raw material for chemical conversion such as materials for synthesizing intermediates for pharmaceuticals and the other chemicals, and a raw material for fermentation in the fields of foods, pharmaceuticals, and general industrial products.

The invention claimed is:

1. A process of producing cellooligosaccharide, comprising enzymatically decomposing, in the presence of cellulase, a water-insoluble natural cellulosic material having an average degree of polymerization not greater than 700, an average particle size not greater than 100 μm, and a diethyl ether-soluble substance content of less than 1% by mass, the water-insoluble natural cellulosic material containing 10% or more by mass of a colloidal cellulose component,
   wherein the cellulase has an activity ratio of 0.5 or less, the activity ratio being a ratio of β-glucosidase activity to crystalline cellulose-decomposing activity at a temperature of 40° C., and
   the cellulase is obtained by culturing a cellulase-producing fungi at a pH of less than 3.5, the cellulase-producing fungi belonging to the *Trichoderma reesei* NBRC31329 strain and the *Trichoderma reesei* GL-1 strain.

2. The process of producing cellooligosaccharide according to claim 1, wherein the water-insoluble natural cellulosic material has an average degree of polymerization not greater than 500 and an average particle size not greater than 50 μm.

3. The process of producing cellooligosaccharide according to claim 1, wherein the water-insoluble natural cellulosic material has an average degree of polymerization not greater than 400 and an average particle size not greater than 30 μm.

4. The process of producing cellooligosaccharide according to claim 1, wherein the water-insoluble natural cellulosic material contains 15% or more by weight of a colloidal cellulose component.

5. The process of producing cellooligosaccharide according to claim 1, wherein the cellulase has an activity ratio not greater than 0.35.

6. The process of producing cellooligosaccharide according to claim 1, wherein the diethyl ether-soluble substance is lignin.

7. The process of producing cellooligosaccharide according to claim 1, wherein the water-insoluble natural cellulosic material contains a cellulose I crystal.

8. The process of producing cellooligosaccharide according to claim 1, wherein the water-insoluble natural cellulosic material has an average particle size not greater than 10.3 μm and contains 40% or more by weight of the colloidal cellulose component.

9. The process of producing cellooligosaccharide according to any one of claims 1, 2 to 4, 5, 7 and 8, wherein the water-insoluble natural cellulosic material comprises 90% or more by mass of a water-insoluble component which is obtained by dispersing a cellulosic material precursor in pure water at 25° C. and removing a water-soluble component by ultrafiltration, the ultrafiltration having a molecular weight cut-off of 10000.

10. The process of producing cellooligosaccharide according to claim 9, wherein the diethyl ether-soluble substance comprises one or more impurities in the natural cellulosic material soluble in diethyl ether, the impurities being selected from a group consisting of lignin and lignin decomposition products, and the diethyl ether-soluble substance content being measured by a method of quantifying a diethyl ether-soluble substance specified by a Purity Test for Crystalline Cellulose (2) in "the Japanese Pharmacopoeia, 14$^{th}$ Edition" published by Hirokawa Publishing.

11. The process of producing cellooligosaccharide according to claim 10, wherein the colloidal cellulose component is expressed as a percentage of a cellulose solid content remaining in a supernatant after dispersing the water-insoluble natural cellulosic material in water to form a water suspension containing 0.2% by mass of the water-insoluble natural cellulosic material, the water-insoluble natural cellulosic material being dispersed with a high-shear homogenizer operated at a speed of 5000 rpm for 3 minutes, adjusting a pH of the water suspension to 7.5 to 8.5, and centrifuging the water suspension with a centrifuge operating at a centrifugal force of 2000 G for 5 minutes.

* * * * *